(12) United States Patent
Gromer et al.

(10) Patent No.: US 8,052,627 B2
(45) Date of Patent: Nov. 8, 2011

(54) SPRAY NOZZLE AND DENTAL CLEANING SYSTEM

(75) Inventors: Oswald Gromer, Heidenheim (DE);
Andreas Kramp, Bad Cambeg (DE);
Michael Sauer, Bad Camberg (DE);
Michael Stolper, Eschborn (DE);
Norbert Schaefer, Frankfurt (DE); Karl Herzog, Frankfurt am Main (DE)

(73) Assignee: The Procter & Gamble Company, Cincinnati, OH (US)

( * ) Notice: Subject to any disclaimer, the term of this patent is extended or adjusted under 35 U.S.C. 154(b) by 1211 days.

(21) Appl. No.: 10/531,484

(22) PCT Filed: Oct. 15, 2003

(86) PCT No.: PCT/EP03/11431
§ 371 (c)(1),
(2), (4) Date: Dec. 9, 2005

(87) PCT Pub. No.: WO2004/034923
PCT Pub. Date: Apr. 29, 2004

(65) Prior Publication Data
US 2006/0097084 A1    May 11, 2006

(30) Foreign Application Priority Data

Oct. 17, 2002 (DE) .................... 102 48 336
Oct. 17, 2002 (DE) .................... 102 48 338
Oct. 17, 2002 (DE) .................... 102 48 339

(51) Int. Cl.
*A61H 9/00* (2006.01)
*A61H 13/00* (2006.01)

(52) U.S. Cl. ........ 601/162; 601/160; 601/169; 239/490; 239/492

(58) Field of Classification Search .......... 601/160–165, 601/169; 433/80; 233/476–477, 482, 488–493; 239/476–477, 482, 488–493, 525, 526, 589
See application file for complete search history.

(56) References Cited

U.S. PATENT DOCUMENTS

| | | | |
|---|---|---|---|
| 2,691,553 A | 10/1954 | Pettigrew et al. | |
| 3,887,137 A * | 6/1975 | Nakamura et al. | 239/468 |
| 4,260,110 A * | 4/1981 | Werding | 239/404 |
| 4,671,463 A * | 6/1987 | Moreland et al. | 601/169 |
| 4,770,632 A | 9/1988 | Ryder et al. | |
| 5,067,655 A * | 11/1991 | Farago et al. | 239/124 |
| 5,152,463 A * | 10/1992 | Mao et al. | 239/402 |
| 5,711,488 A | 1/1998 | Lund | |
| 6,193,172 B1 * | 2/2001 | Soule et al. | 239/468 |
| 2003/0209238 A1 | 11/2003 | Peters | |

FOREIGN PATENT DOCUMENTS

| | | |
|---|---|---|
| DE | 2 041 495 | 4/1972 |
| DE | 27 58 182 | 7/1978 |
| DE | 27 46 453 A1 | 4/1979 |

(Continued)

*Primary Examiner* — Quang D Thanh
(74) *Attorney, Agent, or Firm* — John P. Colbert; Julia A. Glazer; David M. Weirich

(57) ABSTRACT

A dental cleaning system for providing a liquid jet for a mouth rinse includes a nozzle member, a nozzle attachment coupled to the nozzle member to define an axially extending chamber, a liquid duct configured to supply pressurized liquid to the chamber, a pressure piece disposed within the chamber, and a nozzle outlet extending out of the chamber and configured to discharge a cleaning jet.

7 Claims, 15 Drawing Sheets

FOREIGN PATENT DOCUMENTS

| | | |
|---|---|---|
| DE | 28 15 913 | 10/1979 |
| DE | 28 19 404 | 11/1979 |
| DE | 27 46 453 C2 | 3/1987 |
| DE | 199 59 188 | 6/2001 |
| DE | 2 38 191 | 11/2010 |
| EP | 0 066 930 | 12/1982 |
| EP | 1 150 036 | 10/2001 |
| EP | 1 312 418 | 5/2003 |
| FR | 1 491 238 | 8/1967 |
| GB | 233018 | 4/1925 |
| GB | 762230 | 11/1956 |
| GB | 2019961 | 11/1979 |
| GB | 2 087 025 | 5/1982 |
| WO | WO01/41659 | 6/2001 |

\* cited by examiner

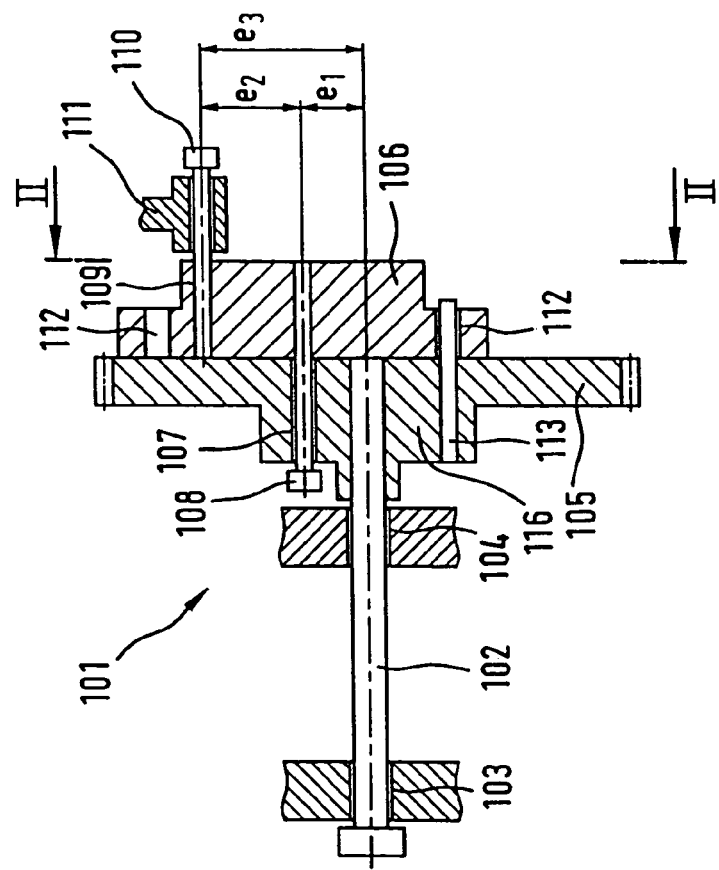
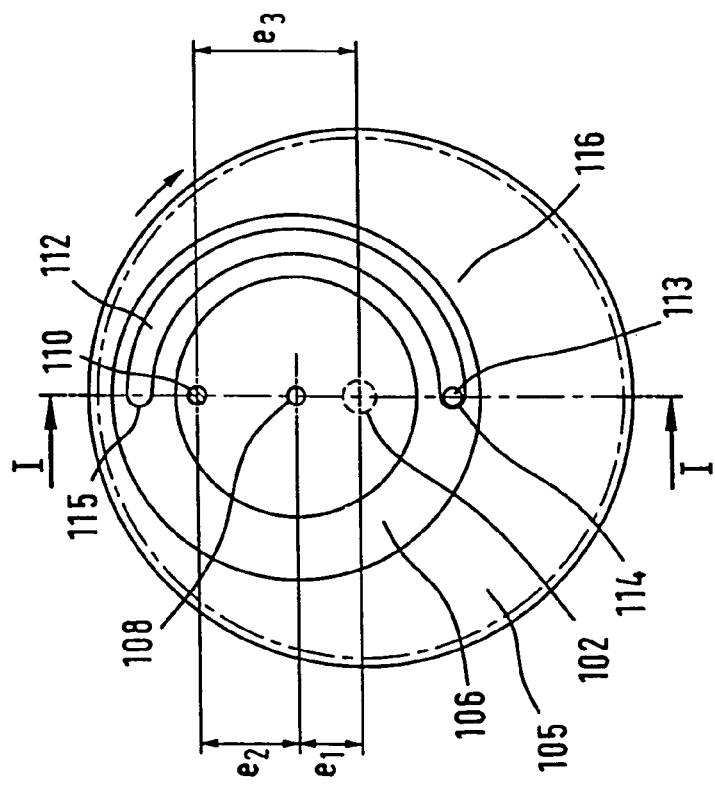
Fig. 9
Fig. 8

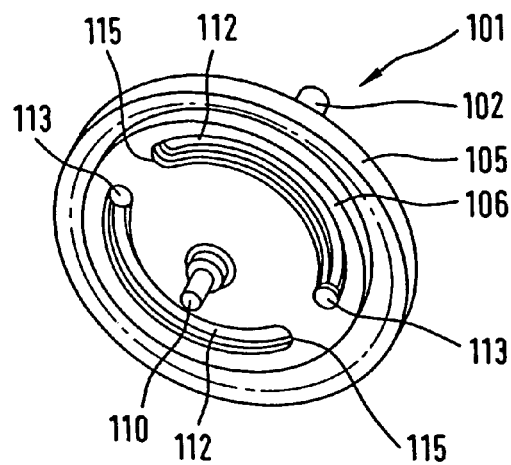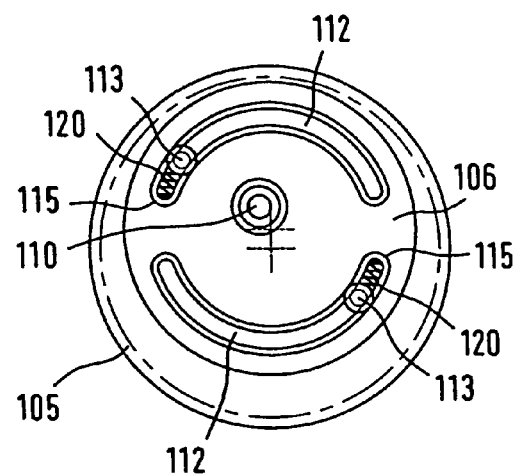
Fig. 12                    Fig. 14
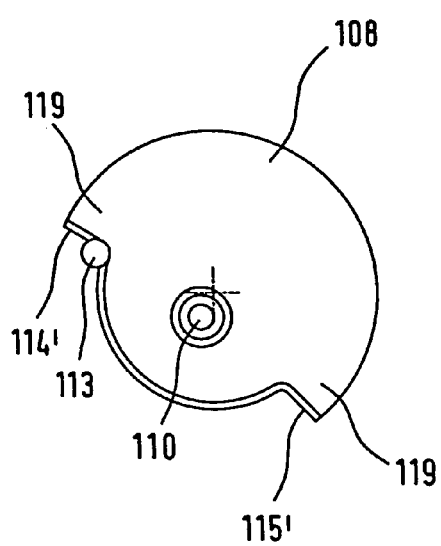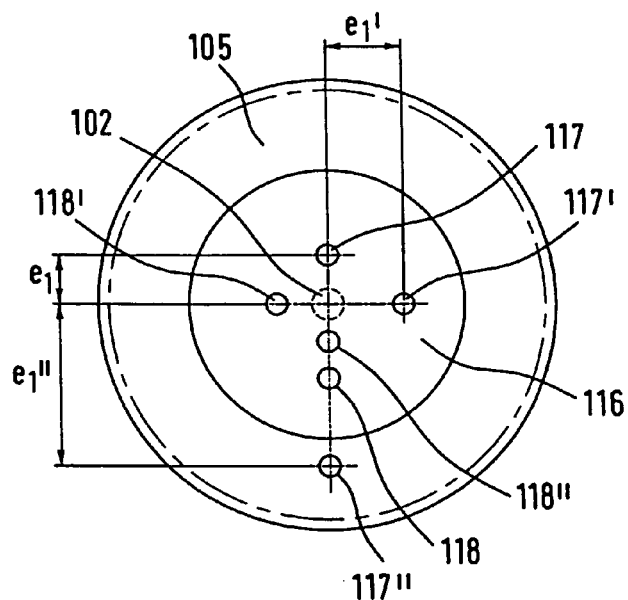
Fig. 13

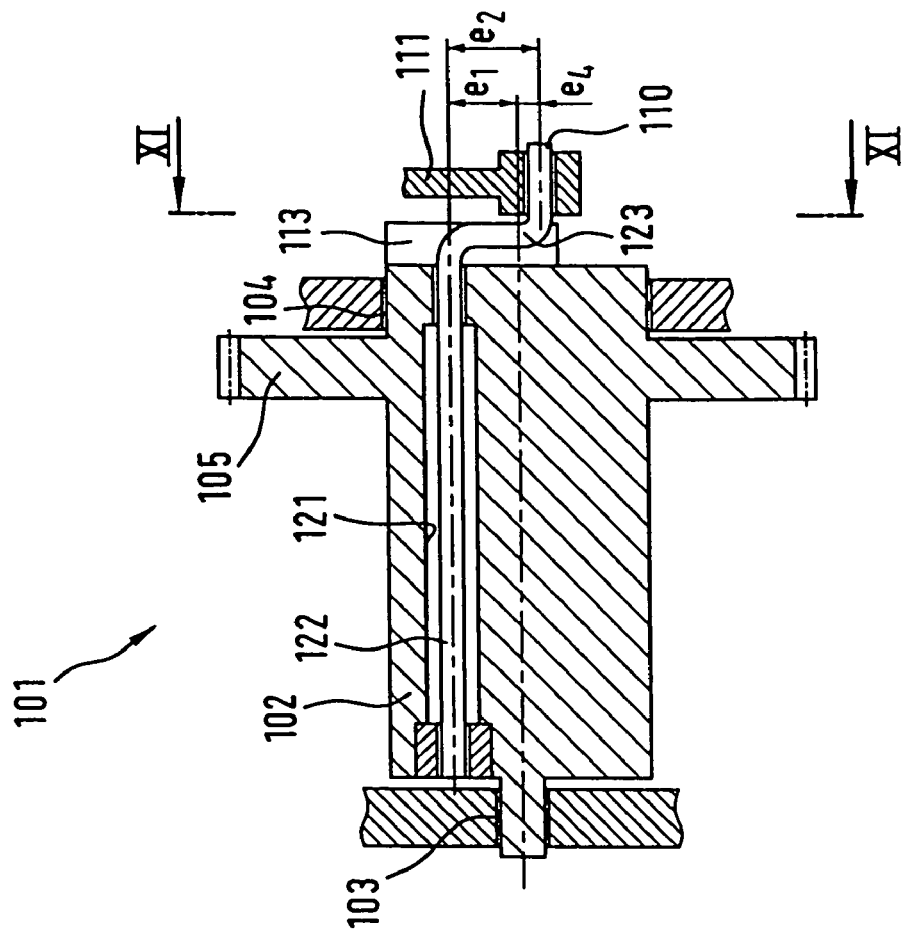
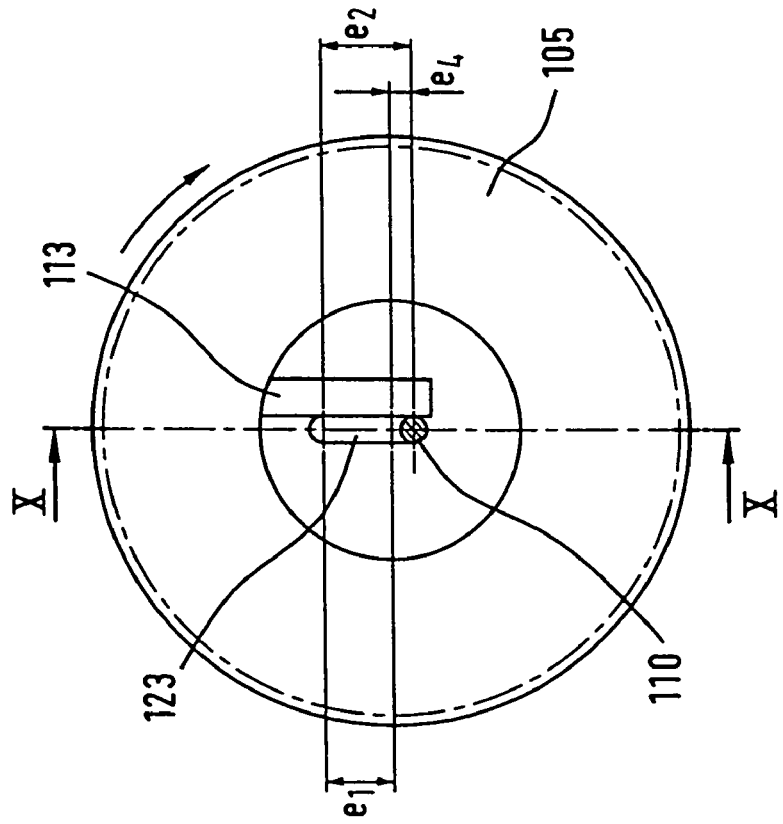
Fig. 17
Fig. 18

SPRAY NOZZLE AND DENTAL CLEANING SYSTEM

TECHNICAL FIELD

This description relates to a mouth rinse, a spray nozzle and a dental cleaning system according to the preamble of the independent claims.

It is known that the cleaning effect of oral rinses is improved by using special spray nozzles to create liquid jets of a specific configuration. EP 0 841 038 A1 discloses an impeller which is arranged in the spray nozzle for rotation about its axis of rotation, being set in rotation by the cleaning liquid that is fed to the impeller. The cleaning liquid passes to the outlet through a duct which is arranged in the impeller at an angle to the axis of rotation. As the result of the rotation of the impeller the cleaning liquid is discharged from the outlet of the spray nozzle in the form of a rotating liquid jet. A single jet is thus created and circulates, evenly distributed, on an expanding cone. In spite of the enlarged effective area, the cleaning effect of a liquid jet created with such a spray nozzle is not optimal as yet. In particular the removal of marginal plaque is possible with such a spray nozzle only to an inadequate degree. Only non-adhering plaque can be removed with the liquid jet of a mouth rinse. The removal of plaque in the approximal region and in the gingival margin is possible only with hand toothbrushes, dental floss or electric toothbrushes, albeit to an unsatisfactory degree. Another disadvantage of the spray nozzle is the rotating impeller, as moving components are subject to greater wear. The longer the use, the greater the wear, and this leads to an enlargement of the bearings, which in turn can result in a reduction of the impeller's speed and ultimately its stoppage.

DE 199 59 188 A1 discloses a dental cleaning device similar to an oral rinse. In addition to a spray nozzle discharging a cleaning liquid, the device needs a cleaning scraper which is configured as a spoon-shaped auxiliary part. A pressure of 3 to 6 bar and an exit velocity of 5 m/s to 15 m/s are provided for the liquid. It is explained that higher values should be avoided as otherwise the liquid jet is perceived as unpleasant. These values are said to be a good compromise between a high cleaning effect and an intensity of impact that is still perceived as pleasant. It is a disadvantage, however, that the scraper is unable to reach into all interproximal spaces and other regions of the teeth.

SUMMARY

According to one aspect, a mouth rinse and a spray nozzle for the mouth rinse which afford an improved cleaning effect. The liquid jet should be capable of removing firmly adhering plaque from the approximal region and the gingival margin. The spray nozzle for creating such a liquid jet should work as far as possible without suffering any wear and be of simple construction. Also, a device enabling extensive cleaning of the teeth and the gums should be provided for the spray nozzle.

According to another aspect, the cleaning liquid is fed at high pressure to a spray nozzle such that a liquid jet comprised of microsized drops is discharged at high velocity from a nozzle outlet. In particular the nozzle outlet forms a thin, fast moving liquid film which is then transformed into microsized drops moving at high velocity.

By providing for the pressure to amount to at least 15 bar and/or the velocity to equal at least 23 m/s the cleaning effect is improved compared to the prior art.

A high pressure of at least 15 bar is sufficient to enable reliable formation of the microsized drops, with the velocity of the liquid jet being preferably higher than 25 m/s. However, a distinctly better cleaning effect is achieved with a pressure of over 20 bar and/or a velocity of over 35 m/s.

In one or more embodiments of the dental cleaning device, it is possible to dispense with a scraper or other auxiliary part. In particular the microsize of the drops is perceived as relatively pleasant. However, in some embodiments, the mouth rinse can be used simultaneously in combination with a brush part or other auxiliary part which contacts the teeth directly. The auxiliary part can be constructed as a ring-shaped brush which is arranged concentrically around the nozzle outlet.

The high impact energy of the drops on the plaque layer causes the cleaning liquid to be deflected sideways. The shear forces generated in the process tear open the plaque surface, forming pits and craters. As the liquid jet is comprised of a multiplicity of drops, this process is repeated in rapid succession. The plaque is thus removed layer by layer. The advantage of a liquid jet which is comprised of drops and created in this manner is that plaque adhering in the approximal region and in the tooth-gingiva junction region can now be removed. Furthermore, on account of the mechanical removal of the plaque layer there is no need for any additive in the cleaning liquid, thus making it possible to use water as cleaning liquid for removing the plaque.

To produce the drops with high velocity the cleaning liquid is fed to the spray nozzle at high pressure. Depending on the special configuration the pressure lies at over 15 bar, approximately, in particular between 25 bar and 55 bar, approximately, with the best cleaning results being achievable in a pressure range from 35 bar to 45 bar.

For the drops to be produced it is necessary for the cleaning liquid to be atomized or sprayed. Particularly small drops can be created with identical nozzle diameters and pressures when the liquid jet is configured as a diverging hollow cone jet. Another advantage of the diverging hollow cone jet is that the spray area becomes larger as the distance from the nozzle outlet increases, thus enabling faster cleaning. However, it is also conceivable to create a solid cone jet or a flat jet apart from the hollow cone jet.

The formation of the jet is decisive, along with the jet shape, for the configuration of the microsized drops. These drops can be created by forming the cleaning liquid in the nozzle outlet as a thin film which is evenly distributed over the inner wall of the nozzle outlet. On leaving the nozzle outlet this evenly distributed film disintegrates shortly after the nozzle outlet into the microsized drops.

Adhering plaque layers can be removed particularly well with a liquid jet comprised of drops with a size of around 5 μm to 10 μm and a velocity of at least 23 m/s, preferably around 45 m/s to 55 m/s.

In one embodiment, the spray nozzle includes a chamber, a liquid duct extending into a chamber and supplying pressurized cleaning liquid thereto, and a nozzle outlet extending from the chamber for discharging a cleaning liquid jet. Advantageously, the chamber is connected to a whirl chamber of approximately round cross section for creating a circulating flow of the cleaning liquid, the nozzle outlet extending centrally from said whirl chamber and being comprised of a preferably approximately cylindrical narrow passage and an optionally adjacent, in particular approximately conical, expansion. The expansion can also be omitted or be constructed with a non-conical shape as required.

With this construction it is possible to create a liquid jet comprised of microsized drops with high velocity, which, owing to the velocity of the drops, is capable of removing dental plaque. A cleaning operation performed with the spray nozzle constructed as a hollow cone nozzle enables in the same period of use a gentler cleaning operation than with an electric toothbrush on account of a distinctly reduced abrasion of the epithelial cell layer. Furthermore, after using an electric toothbrush the spray nozzle of one embodiment provides an additional reduction of approximately 60% plaque particularly in the approximal region. The spray nozzle works without any moving parts, which would be subjected to intensive wear.

A narrow passage in the form of a bore with a diameter of approximately 0.1 mm to 0.2 mm and a depth of approximately 0.05 mm to 0.2 mm has proven to be advantageous for creating the microsized drops with high velocity. A narrow passage of such construction ensures that the cleaning liquid discharged from the whirl chamber enters at high pressure and high velocity into the optionally succeeding expansion.

An expansion, in particular in the form of a cone or hollow cone, has proven to be advantageous for finally forming the liquid jet comprised of many drops, with the expansion following directly on the narrow passage. This atomizer principle enables particularly fine drops to be produced. After the cleaning liquid has passed through the narrow passage it spreads over the wall of the hollow cone as an evenly distributed thin film which rotates around the axis of symmetry of the expansion on account of the whirl chamber. The high tangential velocity causes the film to disintegrate into the microsized drops as soon as it exits from the hollow cone, in particular shortly after the nozzle outlet. A cone or hollow cone with a length of approximately 0.2 mm to 0.5 mm and an opening angle of approximately 20° to 70° has proven to be advantageous for an optimum configuration of the drops. This nozzle geometry also distinguishes itself by enabling small volumetric flows, for example, of less than 80 ml/min, even at high drop velocities, without the nozzle geometry becoming so small that the costs of production increase. Extremely small nozzle geometries, which also have a reduced service life, are thus avoided. Furthermore, the nozzle constructed as a hollow cone has the advantage of displaying a very stable jet profile even in the presence of manufacturing inaccuracies or impurities.

However, the use of a flat jet nozzle or a solid cone nozzle instead of the hollow cone nozzle may also be contemplated.

The outlet can be of compact and hence space-saving construction if it is formed in a nozzle attachment arranged on the nozzle member.

Further contributing to simplifying the production of the nozzle attachment is an arrangement of the narrow passage and the expansion in a separate component, for example, a nozzle plate. Fitting the nozzle plate in the nozzle attachment entails only little additional effort, while production is more favorable with regard to accuracy, dimensional stability and costs. Furthermore, the nozzle plate can be made of a different material that is more resistant to wear.

Replaceability of the nozzle attachment can be configured to detachably connect to the nozzle member for ease of replacement, for example. The detachable connection can be constructed either as a screw connection or as a snap- and push-lock connection, for example, and can thus be replaced, for example in case of damage. At the same time a nozzle member constructed in this fashion enables the accommodation of conventional nozzle attachments, which are operated with a substantially larger volumetric flow at considerably lower pressure.

Advantageously, the chamber includes a pressure piece in the spray nozzle to form a whirl chamber. The pressure piece is arranged in a chamber which is formed between the nozzle attachment and the nozzle member. To fix the pressure piece in the chamber, the part of the pressure piece located in the nozzle member or nozzle attachment is inserted with a press fit or is fixed by means of latching elements arranged on the nozzle attachment or nozzle member. On the one hand this fixing simplifies the mounting, on the other hand the pressure piece is held captive on one of the two parts during any replacement of the nozzle attachment. However, it is also conceivable to hold the pressure piece clamped between the nozzle member and the nozzle attachment through oversize or by means of a spring.

The pressure piece can have a cup-shaped part at each of its ends. The first cup-shaped part faces the narrow passage in the nozzle attachment and forms with its interior space the whirl chamber. The second cup-shaped part faces the liquid duct in the nozzle member.

In the first cup-shaped part provision is made for at least one opening through which the cleaning liquid is allowed to flow from the interior space of the first cup-shaped part into the chamber. A free outflow of the cleaning liquid is ensured when the interior space of the cup-shaped part is in communication with the chamber through at least one opening but preferably through three to four openings.

If the openings are constructed as axial slits through the cup-shaped part, the sections of the cup-shaped part lying between the slits form spring arms which assist the fixing of the pressure piece.

The function of the spring arms is assisted when the pressure piece is made of an elastic material, e.g., a plastics material.

The arrangement of the whirl chamber in the pressure piece as a separate component guarantees a particularly simple production. The whirl chamber is formed by the interior space in the first cup-shaped part, which is mounted on the area around the narrow passage, the narrow passage forming the outlet from the whirl chamber. To seal the whirl chamber, the cup-shaped part is seated around the narrow passage. In one embodiment, the cup-shaped part has a planar seating surface. This type of sealing prevents deformations in the pressure piece. Such deformations could occur with a line-shaped sealing arrangement when the cup-shaped part seals with an edge.

Furthermore it would also be conceivable to construct the sealing faces as a cone. In this construction, the cone angles of the nozzle plate and the pressure piece are configured to be exactly in agreement. By contrast, two plane surfaces afford greater economy of manufacture.

It is also possible to provide, in the area around the narrow passage, detent hooks which cooperate with notches on the outer circumference of the pressure piece in order to ensure the sealing effect. This fixing affords the added advantage of holding the pressure piece captive in the nozzle attachment during a replacement of the spray nozzle.

The access to the whirl chamber is provided by at least one opening in the first cup-shaped part, which opening is perpendicular or at an angle smaller than about 90° to the axis of symmetry of the pressure piece. The configuration of the jet has been shown to be influenced by the number, the cross section and the position of the openings. Good results were obtained with two opposite lying openings which are constructed as slits.

To create a sufficient whirl in the whirl chamber, the openings lead into the whirl chamber approximately transverse to and centrally offset from the longitudinal axis of the whirl chamber. The magnitude of the center offset and the angle at which the openings lead into the whirl chamber are likewise decisive for the jet configuration. For example, a center offset big enough for the liquid jet discharged from the openings to impact on the opposite lying wall of the whirl chamber at an angle smaller than about 45° has proven to be favorable. In this angular range the jet is able to transfer its energy to the developing whirl most effectively.

Feeding the cleaning liquid to the openings takes place through grooves in the first cup-shaped part which extend parallel to the axis of symmetry of the pressure piece. This type of feeding avoids radial feeding, which would require a large space for construction. The spray nozzle can thus be constructed with a small diameter.

A pressure piece with two cup-shaped parts is advantageous when the liquid duct is coaxial with the narrow passage. A spray nozzle with a smaller axial dimension can be achieved when the liquid duct is aligned approximately radially to the narrow passage. With this construction the area facing the liquid duct can be dispensed with, thus simplifying the design of the pressure piece.

On a device including a pump adapted to be driven by an electric motor and a liquid container, in which the pump is connected to a spray nozzle by means of a tube and a hand piece, a spray nozzle according to any one of the device claims is arranged preferably on the hand piece.

If the spray nozzle is arranged on the hand piece of the device so as to be exchangeable for another nozzle, then the device can be operated in various operating modes. The replaceability permits the use of not only the high-pressure spray nozzle for the removal of dental plaque but also, for example, a conventional jet and/or spray nozzle. The spray nozzle is operated with a small volumetric flow at a high pressure, and a standard mouth rinse nozzle with a large volumetric flow at a low pressure. If both nozzles are operated with approximately the same hydraulic power, the pump can be driven by one electric motor, with the pump being of the switchable type using, for example, a switchable gear train.

Switching between the operating modes can take place without additional effort or devices in the hand piece when the nozzle attachment is used for detection of the operating mode to be set. Depending on the nozzle attachment used, a defined pressure builds up in the device. In this case a pressure sensor can be arranged between the pump and the spray nozzle in order to detect the pressure of the cleaning liquid conveyed to the spray nozzle, with a signal indicative of the detected pressure being deliverable from the pressure sensor to a control unit and the electric motor being controllable by the control unit with the operating mode assigned to the detected pressure.

In another construction use is made of the fact that, unlike a conventional jet and/or spray nozzle used in mouth rinse mode, the high-pressure mode with the spray nozzle produces a high torque and a low rotational speed. In this case a rotational speed or torque sensor can be arranged on the pump or on the electric motor in order to detect the rotational speed or the torque of a rotor of the pump or the electric motor, and a signal indicative of the detected rotational speed or the detected torque can be delivered from the rotational speed or torque sensor to a control unit, and the electric motor and/or the pump and/or the gear train can be controlled by the control unit with the operating mode assigned to the detected rotational speed or the detected torque. It will be understood, of course, that the torque and/or the rotational speed can also be detected by means of a measurement taken of the electric current consumed by the motor. In conclusion it can be said that switching between operating modes is possible by detecting the pressure or the electric current.

Particularly advantageous further developments of the mouth rinse, by means of which the mouth rinse can be switched over from a first operating mode to a second another operating mode with lower pressure, will be explained in the following. Provision is herein made for an eccentric shaft or a crankpin to be adjustably arranged in their total eccentric dimension on a drive element, with a crank mechanism being provided for a pump of the mouth rinse, and the mouth rinse being provided with a drive element adapted to be driven for rotation about an axis of rotation by a drive device, and with an eccentric shaft or crankpin, which acts as an output and is arranged on the drive element a total eccentric dimension away from and parallel to the axis of rotation.

As the result of the adjustable total eccentric dimension the output on the crankpin has at least two movements. With these movements it is possible to operate the plunger of a pump with at least two different strokes. In this manner the pump supplies a small delivery volume with a small stroke, while with a large stroke it supplies a large delivery volume. Adjustment takes place by reversal of the drive's direction of rotation.

If the drive element is adapted to be driven for rotation in reversible manner and if the eccentric shaft is arranged on an output element which is arranged on the drive element such as to be freely pivotal between a first and a second end position about a pivot axis arranged a first eccentricity away from and parallel to the axis of rotation, then the adjustment of the eccentricity as the result of a reversal of the direction of rotation on the drive shaft distinguishes itself by a particularly small mechanical effort, whereby the space requirements for the eccentric drive are not substantially increased. No additional locking of the set total eccentric dimension is necessary as the eccentricity depends solely on the direction of rotation. The advantage of this type of adjustment is that the adjustment can take place under load, for example, of the pump. An additional adjusting unit or intervention from the outside to change the eccentricity is not required. The eccentric drive is characterized furthermore by little wear, as the components are moved toward each other only when switching over between the eccentricities, with the switching over usually taking place under no-load conditions.

Setting the eccentricity dependent on the direction of rotation of the drive shaft is particularly easy when the output element has a disk that is mounted on the drive element such as to be pivotal about the pivot axis, when the disk carries a crankpin that extends with a second eccentricity parallel to the pivot axis, and when the drive element has an axially projecting driver that is pivotal with the drive element and projects between two stops defining the two end positions, the stops being arranged on the disk. The driver rests against the respective stop depending on the direction of rotation. The rotation of the disk relative to the drive element depending on the direction of rotation causes the total eccentric dimension of the crankpin relative to the drive element to increase or decrease. By selectively choosing the angular position of the two stops relative to each other it is possible to achieve practically any ratio of small to large total eccentric dimension.

The eccentricities of the disk and the crankpin are likewise variable within wide limits, with the eccentricity of the disk being desirably smaller than that of the crankpin. This ensures that the disk always rests against the driver.

A maximum and a minimum total eccentric dimension of the crankpin relative to the axis of rotation of the drive element is obtainable with a crank mechanism when the stops are arranged such that the eccentricities of the disk and the crankpin are added to or subtracted from each other. The angular distance between the stops on the disk equals 180° in this case. Any variation of the angular position of one or both distances leads to a decrease or increase of one or both total eccentric dimensions depending on the stop changed.

The stops in the disk can be constructed in the form of at least one circular-arc-shaped, concentric groove in which the driver is movable. The ends of the groove then form the stops for the driver in the respective direction of rotation. The groove extends preferably over an angular range of up to 180° and can fully penetrate the disk or be constructed to only a defined depth of the disk.

It is also possible for two or more symmetrically arranged grooves of this type to be constructed in the disk, with a driver being movably arranged in each groove so as to produce a symmetrical support load.

Producing the stops becomes simpler and more economical when they are arranged as regions of the disk with a larger radius.

A particularly good guidance of the disk is achieved by the arrangement of two symmetrically arranged drivers which cooperate with stops that are arranged likewise symmetrically on the disk. Skewing of the disk due to a tilting moment is effectively prevented by the symmetrical engagement. The bending moments and torques as well as the transverse forces from the output-end loading of the crankpin are supported by the stops and/or the disk.

The drivers can be produced particularly easily and hence economically when they are integrally formed on the drive element as studs.

However, it is also possible for the drivers to be arranged as separate components in the form of bolts on the drive element. This configuration has the advantage of the drivers being replaceable.

In another construction, either the stops or the drivers are of the adjustable type. The adjustability can be dependent on the torque, for example. For this purpose the stops are equipped with a spring against which the drivers rest. Depending on the magnitude of the torque generated by the drive device, the stops are displaced by the drivers along the spring travel, thus resulting in a change of the eccentricity. In this way it is possible, in combination with suitable throttling of the conveyed liquid, to fine-tune or individually adapt the stroke of the pump piston, which is produced in dependence upon the direction of rotation, and hence the volumetric flows and pressures. As the result of the dependence on the torque it is possible to set the stroke using a controller of the drive device.

However, it is also conceivable to configure the drivers to be adjustable by means of a spring and to move them against fixed stops.

The spring is, in the simplest case, a spring that is arranged at the respective end of the groove or on the driver. The adjustability can be varied in accordance with the spring characteristic of the spring used.

Helical springs which enable a large spring travel have proven to be favorable for the adjustability within relatively wide limits. Disk springs, leg springs or leaf springs are advantageous for large torques or small spring travels.

The disk is mounted for rotation on the drive element by means of a bolt which is constructed as a separate component. The mounting of the bolt can be dispensed with, however, when it is integrally formed either on the disk or on the drive element.

For mounting the disk the drive element is disk-shaped at one end. The disk is carried in this disk-shaped region. This construction is particularly favorable when the drive element is an injection-molded plastics part.

By configuring the disk-shaped region as a separate component it is possible to provide switchable eccentric drives which are adaptable to various requirements with regard to the volumetric flow and, where applicable, pressure of the liquid to be conveyed. The corresponding disk-shaped region for the requirement has to be mounted, the disk-shaped regions differing solely in the eccentricity of the bearing of the disk and accordingly arranged drivers.

The disk-shaped region can be equipped with several mounts for the disk and accordingly arranged mounts for the drivers, the mounts of the disk having different eccentricities than the drive element. Hence it is possible, with one disk-shaped region and the accordingly selected bearing for the disk, to adapt the eccentric drive or crank mechanism to the respective requirements, thus reducing the diversity of parts.

The drive element can be driven by a drive device via a gear train. A gear is fastened to the drive element for this purpose. The arrangement of the gear on the drive element is easily constructed when the gear is connected to the drive element in one integral piece, preferably by plastic injection molding, or when it forms the drive element. Furthermore, the use of plastic leads to a reduction in the weight of the eccentric drive.

Further contributing to simplifying the drive element is the integration of the disk-shaped region with the bearing of the disk and the drivers in a drive gear, particularly a spur gear of the drive element.

The crank mechanism is of compact construction which can be varied according to requirement. For an axially short design the crank mechanism is disk-shaped, whereas in cylinder design it builds to small radial dimensions. Simple and hence economically produced elements are used when disk- or cylinder-shaped components are employed.

Setting of the total eccentric dimension between the crankpin and the drive element as a function of the direction of rotation of the drive element is achieved in accordance with a second embodiment by a crankpin which is part of a crankshaft eccentrically and rotatably mounted relative to the drive element and by a driver which is arranged on the drive element and limits the turning of the crankshaft relative to the drive element. The eccentricity of the crankpin on the crankshaft is thus superimposed upon the eccentricity derived from the arrangement of the crankshaft relative to the drive element. By turning the crankshaft relative to the drive shaft it is possible to change the eccentricity of the crankpin relative to the drive shaft. Turning of the crankshaft relative to the drive element takes place with each change of the direction of rotation on the drive element, the crankshaft only being able to turn relative to the drive element within the limits of the driver.

The eccentricities resulting from the arrangement of the crankshaft relative to the drive element and from the configuration of the crankpin on the crankshaft are variable within wide limits, with the eccentricity of the crankshaft relative to the drive element being preferably smaller than that of the crankpin. It is thereby ensured that the crank web invariably rests against the driver.

The eccentricities arising as the result of the direction of rotation are determined by the arrangement of the driver on the drive element. In a particularly simple construction the driver is a radially extending bar which acts on the crank web of the crankshaft.

The arrangement of the driver is particularly simple to construct when it is integrally formed on the drive element.

A maximum and a minimum total eccentric dimension of the crankpin relative to the drive element are achieved when the crank web is driven by the driver in a radially outward pointing position and a radially inward pointing position. In this arrangement the two positions and the bearing of the crankshaft are on one line. The driver is arranged likewise with a nearly radial orientation.

If the eccentricity of the crankshaft is greater than the radius of the drive element caused by the acting forces and moments, the bearings of the crankshaft lie alongside the drive element. Therefore, the drive element and the crankshaft have to be joined together in suitable manner. The unbalance of the drive element produced thereby is avoided when the radius of the drive element is selected large enough for the bearing of the crankshaft to lie inside this radius.

Advantageously, a piston of a pump of the mouth rinse can be axially slidably and guided in two relatively spaced bearings of the pump housing.

Hence the bearings inside the pump housing are positioned toward the piston ends. The shortening of the regions of the piston projecting beyond the bearings achieved thereby leads to a reduction of the static and dynamic loads on the bearings and the piston on account of the now smaller transverse forces acting on the piston ends.

A further reduction of the loads in the bearings is achieved when at least one of the bearings is arranged in an end region of the displacement path of the piston in the pump housing. This enables for this particular bearing the moments to be reduced practically to zero, thus limiting the loads to the action of forces. Particularly little expenditure is involved when the pump chamber is constructed as the bearing site. It is also conceivable to implement the bearing on the piston end of a sliding-block guideway. For this purpose the pump housing is expanded so that preferably the cover faces of the sliding-block guideway are accommodated by the housing. The bearing is constructed in accordance with FIG. 23 such that it fully accommodates the cover faces of the sliding-block guideway as the piston end, the bearing having an axial dimension that is larger than the stroke of the piston. It is thus guaranteed that the cover faces of the sliding-block guideway are invariably in the area of the bearing.

A large bearing receiving the cover faces of the sliding-block guideway is avoided when the sliding-block guideway is not arranged at the end of the piston but, as shown in FIG. 24, between the two ends of the piston. In this way it is possible to obtain a bearing which is substantially smaller in diameter. Any unfavorable bearing forces which may arise depending on the application are negligible.

The crankpin can be mounted for rotation in a sliding block which is movably arranged in a direction transverse to the direction of movement of the piston in a sliding-block guideway connected to the piston.

Mounting the crankpin in a sliding block with bore ensures on the one hand a relatively fast and extensive connection of the moved crankpin to another component. In this way the high surface pressure of the crankpin against another component is reduced. In spite of the still large relative movement between the sliding-block guideway and the sliding block, the surface pressure against the piston is substantially reduced on account of the very large surface compared to a crankpin, which has a positive effect on the service life of the components concerned. Furthermore, the loads of other components, particularly those of the bearing sites of the piston and the seal, are also reduced.

With the smaller friction forces and friction moments it is possible to reduce the motor power, thus reducing the current input to the pump or enabling a smaller motor to be used. Also, the reduced load permits the crankpin to be constructed with a smaller diameter, which contributes likewise to reducing the friction. On the other hand the planar support enables greater force transmission, which means that such a pump can be designed to accommodate higher pressures.

A reduction of the load is also achieved by fabricating the sliding block and the sliding-block guideway from a material pair with low friction.

A further reduction of the surface pressures is achieved by providing for a cardan coupling between the piston and the crankpin. It is thus possible to compensate in particular for production-induced or assembly-induced tolerances and/or deformations which lead to a spatially skewed arrangement of the crankpin relative to the piston.

A particularly simple construction of the cardan or cardan-type arrangement is accomplished when the sliding block has a cylindrical cross section and the sliding-block guideway is constructed as a bore with a corresponding cross section in a part formed fast with the piston such that the sliding block is arranged to rotate about its own longitudinal axis. This movability permits the movement about one axis to be compensated for. Another essential advantage of the cylindrical sliding block is that the entire outer surface of the sliding block is in contact with the sliding-block guideway. This configuration distinguishes itself by an extremely low surface pressure. The components have a long life on account of the low specific loads.

Like the cylindrical sliding block, the piston is also mounted for rotation about its longitudinal axis. This enables the sliding-block guideway to perform a compensation movement about a second axis. Hence the interaction of movements by the sliding block and the sliding-block guideway guarantees a compensation of movement about two axes, which is necessary for compensating for the tolerances of a spatially skewed crankpin.

Additional friction between the crankpin and the sliding-block guideway is avoided when an elongated hole is constructed in the wall of the sliding-block guideway for the crankpin to pass through, said elongated hole having a greater width than the diameter of the crankpin. With an elongated hole constructed like this, unwelcome friction is avoided particularly with a spatially skewed crankpin.

To further reduce the friction between the crankpin and the sliding block it is suitable to mount the crankpin for rotation in the sliding block in a bearing which is inserted in a bore of the sliding block. The bearing is constructed preferably as a sliding bearing. Through a suitable choice of material the friction can be reduced still further. In addition to cast or wrought alloys, plastics are an advantage in particular when the requirements are not too high. Plastics have good sliding and antifrictional properties and are characterized by good lubrication.

The eccentric drive or crank mechanism can have a drive shaft, and the eccentricity of the crankpin relative to the drive shaft of the eccentric drive can be adjustable. This construction enables the crankpin to be switched over to another eccentricity with which a different piston stroke can be achieved. This enables the pump to be used in two operating modes.

The pump inlet and/or the pump outlet can be arranged axially to the longitudinal dimension of the pump chamber.

However, it is also possible for the pump inlet and/or the pump outlet to be arranged radially to the pump chamber, whereby they can be arranged radially one beside the other.

It is also possible, however, for the pump inlet and pump outlet to be arranged axially one behind the other.

When in this case the piston or the wall of the pump chamber has a longitudinal groove or flattening through which at least one of the ports is connected to the pump chamber, then this ensures a connection of the ports to the pump chamber independently of the position of the piston.

Non-return valves arranged in the ports make sure that the pump inlet and pump outlet are closed depending on the movement of the piston.

The seal can be arranged between the bearings of the piston such that it radially encloses the piston. The direct ingress of wear particles is greatly reduced by this decoupling of bearing and seal. This leads to a material reduction of wear on the seal. The smaller amount of wear prolongs the life of the seal without any accompanying pressure reduction in the pump chamber.

The seal is subjected to particularly small loads when it is arranged centrally between the bearings. Particularly with an off-center position of the sliding block relative to the piston axis, the seal is exposed to only minor radial loads by tilting moments.

A further reduction in the ingress of wear particles from the bearings is achieved when in the region between the bearings the piston has a larger or a smaller diameter than in the area of the bearings.

In one embodiment, the seal is fixed in the pump housing and includes a sealing lip which radially encloses the piston and is in sealing engagement with it.

A weakening of the piston diameter by a circumferential groove is thus avoided. This construction enables the piston to be dimensioned with a smaller diameter because of the absence of the circumferential groove. This enables a reduction in the required space and in the masses moved in oscillating fashion.

DESCRIPTION OF THE DRAWINGS

FIG. 8 is a sectional view of a first embodiment of an eccentric drive or crank mechanism of the mouth rinse, taken in the plane I-I of FIG. 9;

FIG. 9 is a sectional view of the eccentric drive, taken in the plane II-II of FIG. 8;

FIG. 12 is a perspective view of the eccentric drive similar to FIG. 8 with two drivers;

FIG. 13 are views of a spur gear and a disk of the eccentric drive;

FIG. 14 is a view of a crank mechanism with variable stops;

FIG. 17 is a sectional view of the eccentric drive of FIG. 15 with the direction of rotation changed, taken in the plane X-X of FIG. 18;

FIG. 18 is a sectional view of the eccentric drive, taken in the plane XI-XI of FIG. 17;

DETAILED DESCRIPTION

Figure 1:
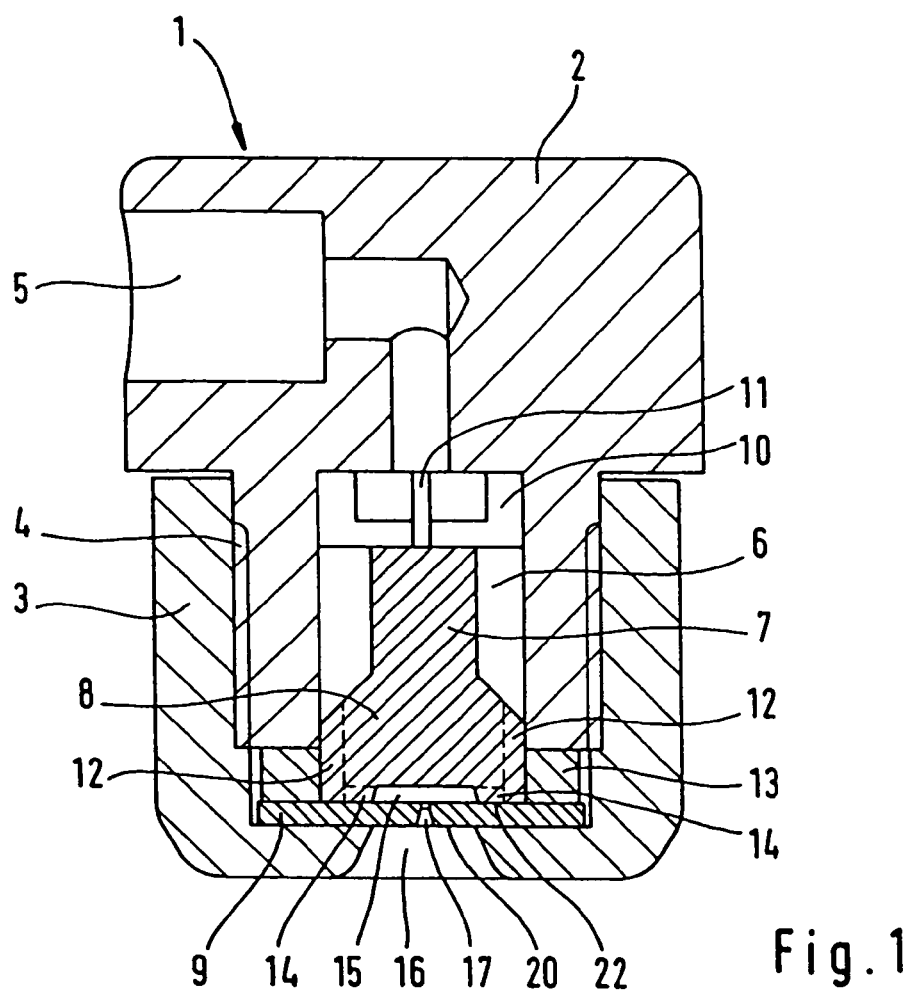
FIG. 1 is a sectional view of a spray nozzle illustrating a first embodiment.

The spray nozzle 1 shown in FIG. 1 is comprised of a nozzle member 2 which is connected to a nozzle attachment 3 by means of a screw connection 4. Arranged in the nozzle member 2 is a liquid duct 5 for the cleaning liquid.

The nozzle member 2 combines with the nozzle attachment 3 to form a chamber 6 into which the liquid duct 5 leads. Inserted in this chamber 6 is a pressure piece 7.

The pressure piece 7 is constructed to be radially expanded and cup-shaped at its two ends. With the first cup-shaped part 8 the pressure piece 7 sits on a nozzle plate 9. The second cup-shaped part 10 encompasses the area in which the liquid duct 5 leads into the chamber 6.

The second cup-shaped part 10 has four evenly distributed axial slits 11 through which cleaning liquid conveyed in the liquid duct 5 is allowed to flow into the chamber 6.

The first cup-shaped part 8 has two grooves 12 formed axially on the circumference of the pressure piece 7. In the area of the grooves 12 the cup-shaped part 8 is encompassed by a ring 13. This ring 13, which can be made of polyamide in one example, seals off the circumference of the cup-shaped part 8 such that the grooves 12 act as ducts. Adjoining the lower end of the grooves 12 and extending radially thereto are ducts 14 formed as slits which extend approximately tangentially into a whirl chamber 15.

The whirl chamber 15 is formed by the space in the interior of the first cup-shaped part 8 and by the nozzle plate 9. At the same time, the nozzle plate 9 closes an opening 16 in the nozzle attachment 3.

The nozzle plate 9 in turn has a passage 17 through which the cleaning liquid exits the whirl chamber 15.

Figure 2:
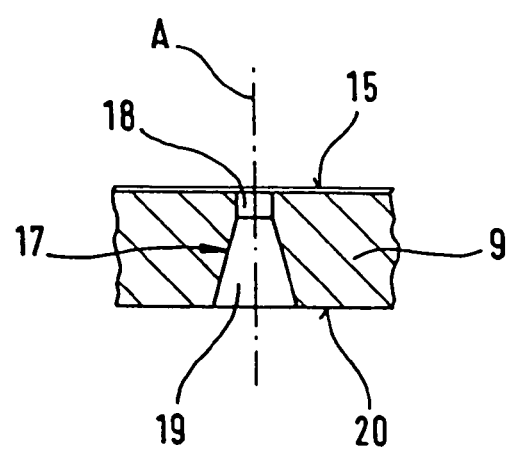
FIG. 2 is a view of the nozzle plate of FIG. 1 on an enlarged scale.

In FIG. 2 the passage 17 of the nozzle plate 9 is shown on an enlarged scale. The passage is comprised of a bore 18 which forms the outlet from the whirl chamber 15. The bore 18 has a diameter of, for example, 0.15 mm and a length of, for example, 0.11 mm.

Adjoining the bore 18 is a diverging hollow cone 19. The hollow cone 19 has an opening angle of, for example, 30° at a length of, for example, 0.35 mm.

The cleaning liquid set in rotation in the whirl chamber 15 by the approximately tangential ducts 14 is greatly accelerated in a whirling pattern as the result of the small diameter of the bore 18. The cleaning liquid then enters the hollow cone 19. In the hollow cone 19 the cleaning liquid develops an evenly distributed film over the wall of the hollow cone 19 as the result of the whirling movement and the decompression. At the same time the film rotates about the axis A at high velocity. When the thus moving cleaning liquid reaches the edge 20, the film disintegrates into a multiplicity of drops with an average size of around 10 μm, which move with a velocity of around 50 m/s. The aggregate of the drops disperses from the edge 20 to form a substantially conical pattern.

Figure 3:
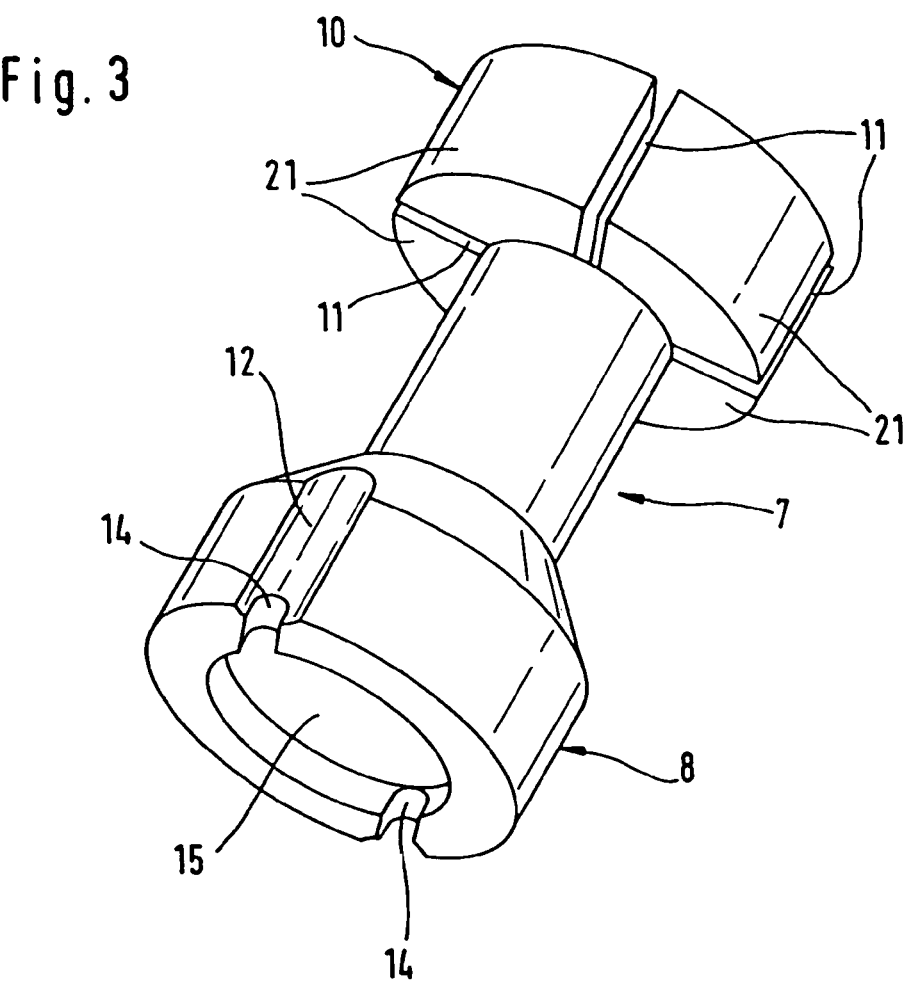
FIG. 3 is a perspective view of the pressure piece of FIG. 1.

The pressure piece 7 in FIG. 3 shows the two cup-shaped parts 8, 10. The second cup-shaped part 10 is divided into four sections by four slits 11 which are evenly distributed around the circumference. On account of their form these sections act as spring arms 21. The spring arms 21 bear against the nozzle member 2 such that the first cup-shaped part 8 is urged with the face 22 against the nozzle plate 9.

Arranged on the circumference of the first cup-shaped part 8 are the two grooves 12. The grooves 12 are each adjoined by a duct 14, which lead approximately tangentially straight into the whirl chamber 15. Through the grooves 12 and the ducts 14 the cleaning liquid flows from the chamber 6 to the whirl chamber 15.

Figure 4:
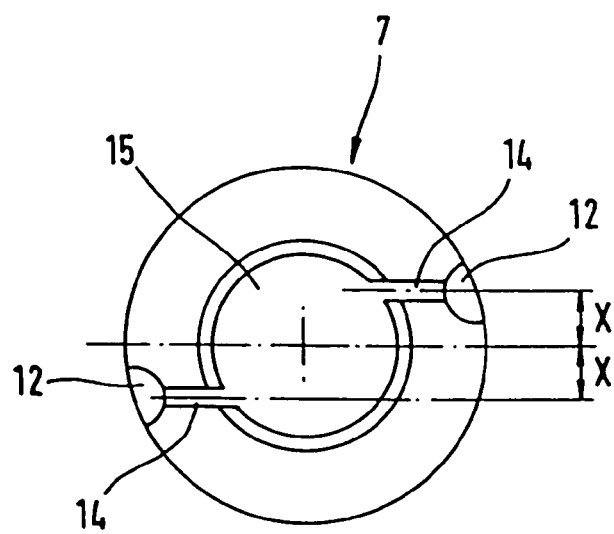
FIG. 4 is a top plan view of the whirl chamber of FIG. 1.

The position of the ducts 14 in relation to the whirl chamber 15 becomes apparent from FIG. 4. The ducts 14, rather than leading radially from the grooves 12 to the center, extend in opposite directions in parallel with each other, entering the whirl chamber 15 with a center offset X. The center offset is selected such that a jet entering the whirl chamber 15 without interference impacts on the wall of the whirl chamber at an angle smaller than 45° and is diverted on the wall into a circulating current.

Figure 5:
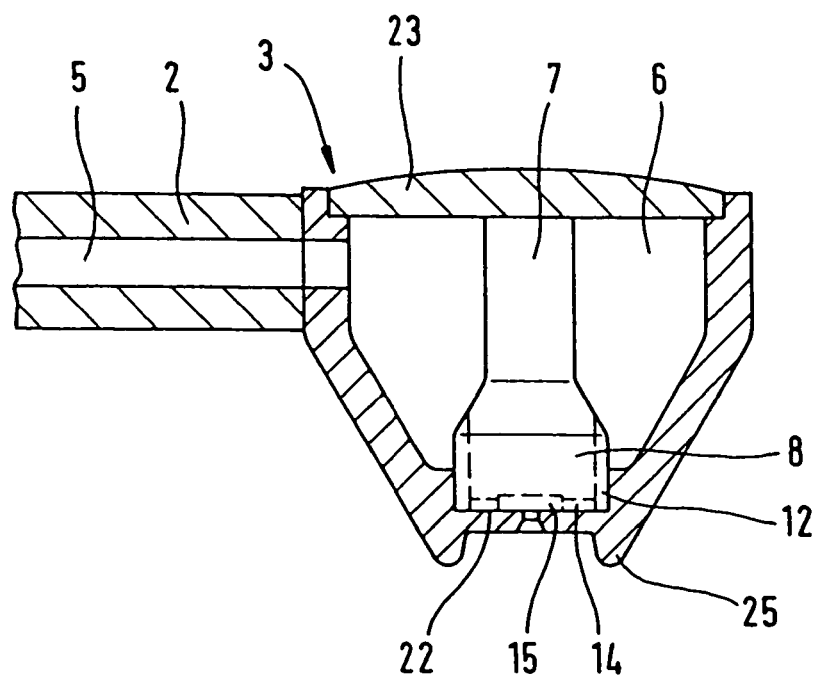
FIG. 5 is a sectional view of a spray nozzle illustrating a second embodiment.
Figure 6:
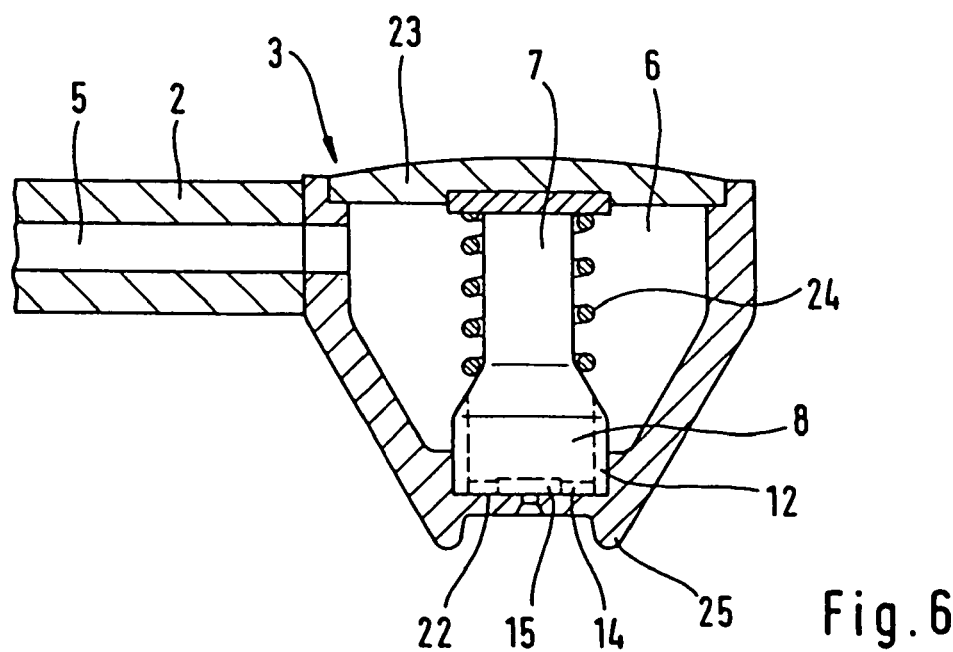
FIG. 6 is a sectional view of a spray nozzle illustrating a third embodiment.

FIGS. 5 and 6 show a second embodiment of the spray nozzle 1. The nozzle member 2 is arranged, in relation to the axis of symmetry of the nozzle attachment 3, not radially but preferably approximately tangentially on the nozzle attachment 3. Hence the liquid duct 5 leads into the chamber 6 likewise from the side. The chamber 6 is closed with a cover 23.

The pressure piece 7 is simplified inasmuch as no second cup-shaped part is necessary. The whirl chamber 15 is arranged again in the first cup-shaped part 8. In FIG. 5 the pressure piece 7 takes support upon the cover 23 such that the face 22 rests with a sealing effect on the nozzle attachment 3. In FIG. 6 the sealing effect of the face 22 is assisted by a spring 24 which urges the pressure piece 7 against the nozzle attachment 3.

The cleaning liquid again reaches the whirl chamber 15 through grooves 12 and slits 14 which are arranged similar to FIGS. 1 to 4. In contrast to FIG. 1 the spray nozzles 1 of FIGS. 5 and 6 have no nozzle plate. The bore 18 and the hollow cone 19 are arranged in the nozzle attachment 3. Provided on the nozzle attachment 3 are several extensions 25 formed around the exiting jet. The extensions 25 have an axial dimension of 3 mm, approximately. The extensions 25 are used for setting an optimum working distance in that the spray nozzle 1 is placed with the extensions 25 on the regions to be cleaned.

Figure 7:
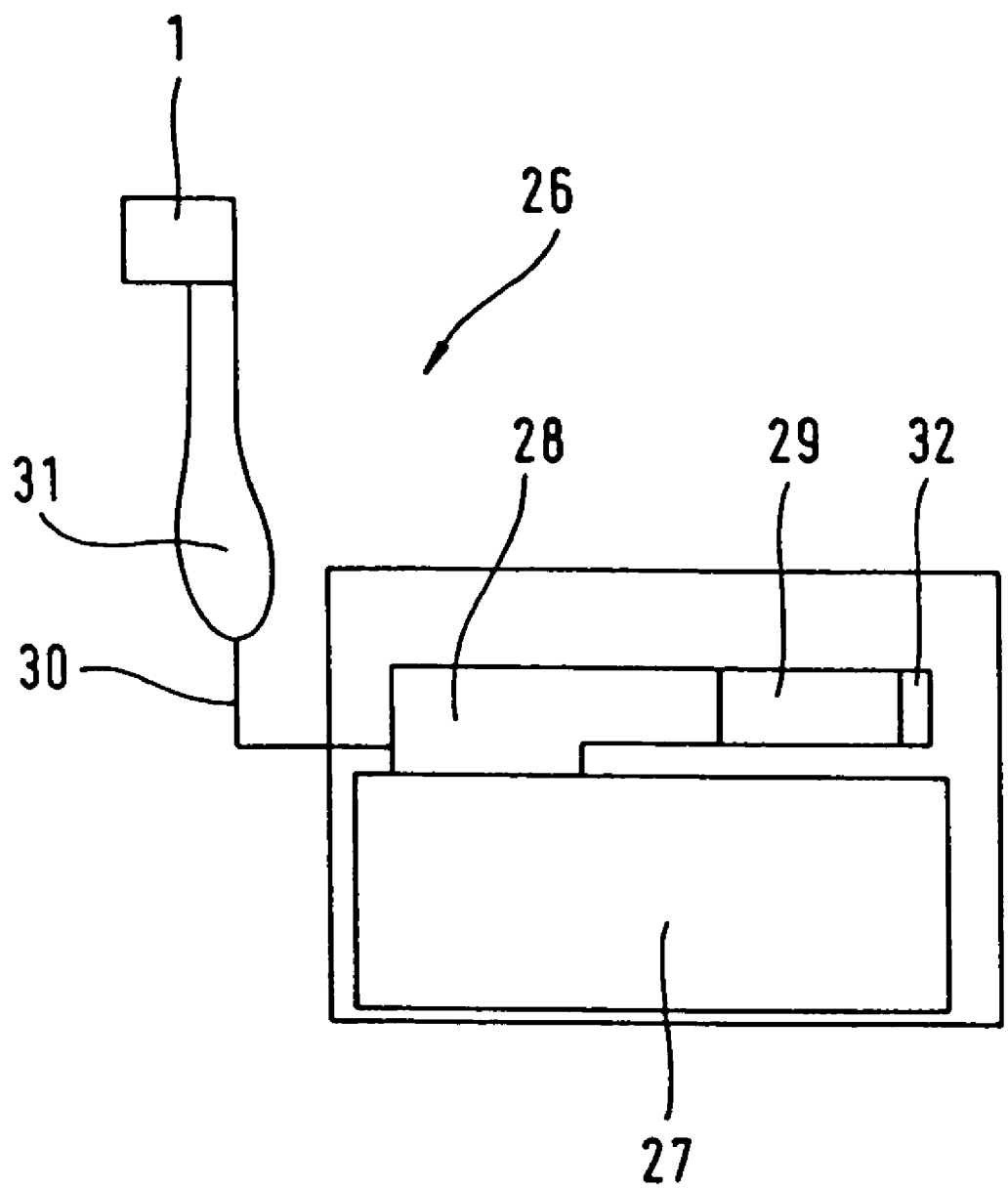
FIG. 7 is a view of a device with a spray nozzle.

The device 26 of FIG. 7 includes a liquid container 27 which can be filled with cleaning liquid by the user. The cleaning liquid is conveyed out of this liquid container 27 through a tube 30 to a hand piece 31 by means of a pump 28 which is powered by an electric motor 29. The spray nozzle 1 is replaceably arranged on the hand piece 31. Arranged on the electric motor 29 is a sensor 32 which measures the torque generated by the electric motor 29 and then sends a signal to the pump 28 so that the latter can be operated in the operating mode which corresponds to the spray nozzle used.

In use, the pump 28 generates in high-pressure mode a volumetric flow of 50 ml/min at approximately 40 bar. This is roughly equivalent to a mechanical or hydraulic output of 2,000 ml/min bar, approximately, or 3.3 W, approximately. When a conventional spray nozzle is arranged on the hand piece 31, the sensor 32 detects the changed torque compared with the spray nozzle 1, and the pump 28 is operated in mouth rinse mode. In this case the pump 28 delivers a volumetric flow of 300 ml/min, approximately, with a pressure of 6 bar. This results in a mechanical or hydraulic output of 1,800 ml/min bar, approximately, or 3.0 W. With the mechanical output in both operating modes being approximately equal, it is possible to operate the device 26 with a pump 28 and an electric motor 29.

Description of Crank Operation for the Mouth Rinse

The eccentric drive described in the following has at least two different movements at the output. The different movements at the output can be set with minimum expenditure. Adjustment is possible furthermore without any outside intervention in the drive. The space required for the eccentric drive is not significantly larger.

The eccentric drive 101 of FIG. 8 has a drive element 102 which is constructed as a drive shaft and carried in two bearings 103, 104. Fastened to one end of the drive shaft is a spur gear 105. The spur gear 105 is connected to a drive device, not shown, and is used for driving the drive shaft. A disk-shaped region 116 for receiving a disk 106 is integrated in the spur gear 105. For this purpose the spur gear 105 has a bore 107 arranged with an eccentricity e1. The disk 106 is rotatably mounted in the bore 107 with a pin 108. The disk 106 has a bore 109 arranged with an eccentricity e2, in which is inserted a crankpin 110 acting as an output device. Acting on the crankpin 110 is a connecting rod 111 which drives the piston, not shown, of a pump. The disk 106 has a groove 112 which is engaged by a driver 113 constructed as a bolt that is fastened in the spur gear 105.

In the representation shown in FIG. 8, the disk 106 and the crankpin 110 are arranged such that the eccentricities e1 and e2 of the disk and of the crankpin, respectively, are oriented in a line. In this position the eccentricities e1 and e2 add up to the largest total eccentric dimension e3. The crankpin 110 transfers to the connecting rod 111 a stroke equal to twice the total eccentric dimension e3.

FIG. 9 shows the spur gear 105 with the disk 106 arranged eccentrically on it and the crankpin 110 arranged eccentrically to the disk 106. The driver 113 fastened to the spur gear 105 engages in the circular-arc-shaped groove 112 of the disk 106. The groove 112 extends over an arc of 180°. The ends 114, 115 form the stops for the driver 113. The largest total eccentric dimension e3 is obtained when the spur gear 105 is driven in the shown direction of rotation. The driver 113 runs in the groove 112 of the disk 106 as far as the stop 114. When the driver 13 abuts the stop 114, the disk 106 rotates in the direction of rotation shown, and with it the crankpin 110 with the spur gear 105.

Figure 11:
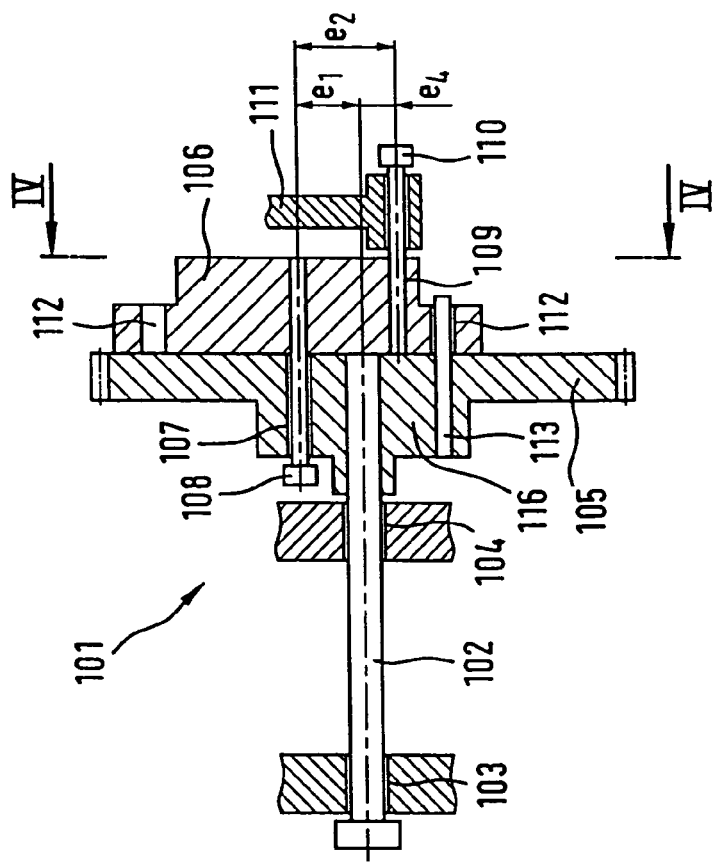
FIG. 11 is a sectional view of the eccentric drive, taken in the plane III-III of FIG. 10.
Figure 10:
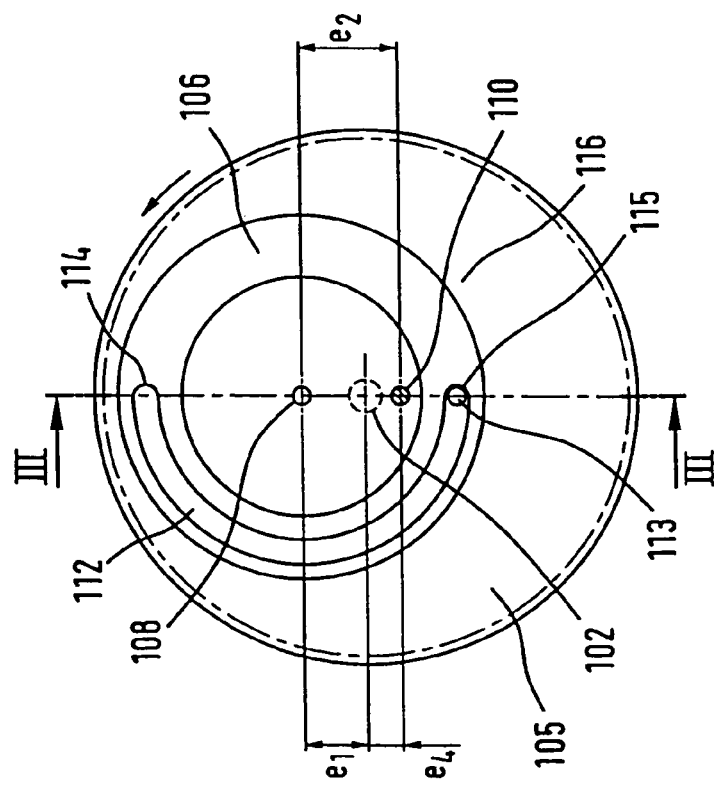
FIG. 10 is a view of the eccentric drive of FIG. 8 with the direction of rotation changed, taken in the plane IV-IV of FIG. 11.

FIGS. 10 and 11 show a changed position of the crank mechanism 101 of FIGS. 8 and 9, the spur gear 105 being driven in the opposite direction of rotation. On its end close to the disk 106, the drive shaft has a disk-shaped region 116 designed to receive the disk 106. The spur gear 105 is arranged on the circumference of the disk-shaped region 116.

Upon switching over to the direction of rotation shown, the connecting rod 111 counteracts with a braking moment such that the crankpin 110 and hence the disk 106 persist in their position. The driver 113 arranged in the spur gear 105 now runs from the stop 114 in the groove 112 to the stop 115 such that the spur gear 105 rotates through an angle of 180° relative to the disk 106. As soon as the driver 113 abuts the stop 115, the disk 106 is driven along by the driver 113. The spur gear 105 and the disk 106 rotate again at the same rotational frequency.

As the result of the spur gear 105 rotating through an angle of 180° relative to the disk 106, the eccentricity e2 of the crankpin 110 acts against the eccentricity e1 of the disk 106. The smallest total eccentric dimension e4 is obtained. The crankpin 110 now only transfers to the connecting rod 111 a stroke that is equal to twice the smallest total eccentric dimension e4.

The crank mechanism 101 of FIG. 12 shows an eccentric drive 101 that is slightly different compared to FIG. 8, with the toothed ring of the spur gear 105 being illustrated as a dot-and-dash line. The spur gear 105 has two symmetrically arranged drivers 113 which run in two concentrically arranged circular-arc-shaped grooves 112 in the disk 106. The ends of the grooves 114, 115 form the stops for the drivers 113.

The eccentric drive 101 shown in FIG. 13 has a spur gear 105 whose toothed ring is shown as a dot-and-dash line. The spur gear 105 has several bores 117, 117', 117". These bores 117, 117', 117" serve to mount the disk 106, with the bores 117, 117', 117" having different eccentricities e1, e1', e1". Hence the spur gear 105 can be used for various requirements by mounting the disk 106 in the corresponding bore 117, 117', 117". Associated with the bores 117, 117', 117" are corresponding bores 118, 118', 118" in which the driver 113 is arranged.

The disk 106 again has stops 114', 115' which however are not arranged in the disk 106 as grooves 112 but as regions 119 with a larger radius on the circumference of the disk 106.

The disk 106 of FIG. 14 has two concentrically arranged grooves 112 in which two drivers 113 run. One helical spring 120 is arranged respectively at the ends of the grooves 112 such that depending on the direction of rotation of the drive shaft each driver 113 rests against a helical spring 120 and the disk 106 rotates at the rotational frequency of the drive shaft. The helical springs 120 have the effect of preventing the drivers 113 from resting against the very end of the respective groove 112. Therefore, the crankpin 110 no longer lies on a line with the center of the disk 106 and the drive shaft, and the eccentricity e1 is added only in part to the eccentricity e1 of the disk 106. The resulting largest total eccentric dimension e3 is thus smaller. In addition, shocks upon changing the direction of rotation are cushioned.

The helical springs 120 are constructed with regard to their spring characteristic such that even minor changes of the torque generated by the drive device are sufficient to change the spring travel by way of the drivers 113 transmitting the torque. With changes of the spring travel the disk 106 turns relative to the drive shaft, thus producing minor changes in the position of the crankpin 110 and hence in the total eccentric dimension e3, e4. With a torque controller on the drive device or the drive shaft it is thus possible to finely adjust the total eccentric dimension e3, e4 and hence the stroke of the connecting rod.

Figure 15:
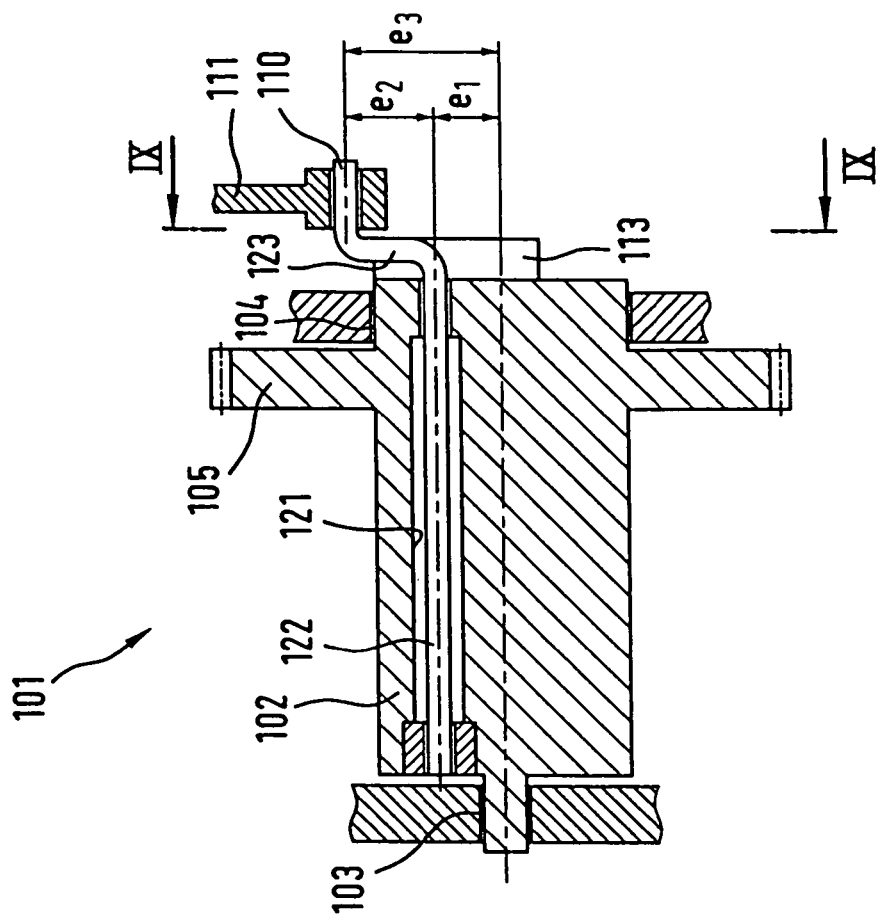
FIG. 15 is a sectional view of a second embodiment of an eccentric drive or crank mechanism, taken in the plane VIII-VIII of FIG. 16.

In a second embodiment of the eccentric drive 101 of FIG. 15 the spur gear 105 and the drive shaft are a single-piece construction forming a drive element 102. The drive shaft is rotatably mounted in the bearings 103, 104. The drive shaft has a bore 121 carrying a crankshaft 122. The crankshaft 122 is arranged with an eccentricity e1 in the drive shaft. The crankpin 110, which is connected by way of a crank web 123 to the crankshaft 122, has an eccentricity e2 relative to the crankshaft 122. Fastened to the crankpin 110 is the connecting rod 111.

In the presentation shown, the crankshaft 122 is arranged such that the crankpin 110 is orientated in a radially outward direction relative to the bearing of the crankshaft 122. In this position the eccentricities e1, e2 of the crankshaft 122 and the crankpin 110 add up to the maximum total eccentric dimension e3. The crankpin 110 transfers to the connecting rod 111 a stroke equal to twice the total eccentric dimension e3.

Figure 16:
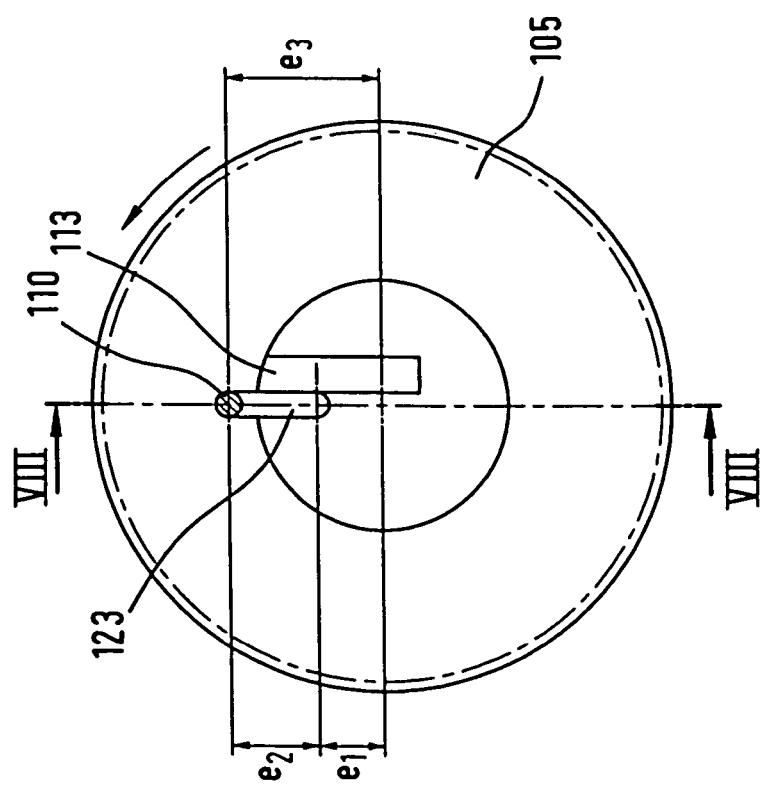
FIG. 16 is a sectional view of the eccentric drive, taken in the plane IX-IX of FIG. 15.

In the sectional view of the eccentric drive 101 of FIG. 16 the drive element 102 is driven in the direction of rotation shown by the drive device, not shown, via the spur gear 105. A driver 113 integrally formed on the drive element 102 is arranged such that it entrains the crankshaft 122 in the position shown in FIG. 15.

FIGS. 17 and 18 show the arrangement of the eccentric drive 101 of FIGS. 15 and 16, the spur gear 105 being driven in the opposite direction of rotation. Upon changing the direction of rotation, the crankshaft 122 rotatably arranged in the drive shaft rotates through 180°. The crankpin 110 is arranged in a radially inward direction relative to the bearing of the crankshaft 122 such that its eccentricity e2 is now orientated in opposition to the eccentricity e1 of the crankshaft 122. The smallest total eccentric dimension e4 is thus obtained between the crankpin 110 and the drive element 102. The crankpin 110 transfers to the connecting rod 111 a stroke equal to twice the smallest total eccentric dimension e4.

At this point it should be noted, in particular with reference to FIGS. 10, 11, 17, 18, that the sub-eccentricities are not shown to scale in magnitude and direction. It is preferred rather to provide for being able to select the eccentricity e2 larger than the eccentricity e1. This means that when the small eccentric dimension e4 is set, then the drive-end driver 113 rests against the stop 115 in every position of rotation.

Such a crank mechanism can be used not only for mouth rinses but can also be applied to other fields including, for example, pump devices in general or devices on which a rotary movement is to be converted into a translational movement.

Description of the Plunger Pump of the Mouth Rinse

The mouth rinse has a plunger pump. This pump displays a better degree of efficiency compared to known mouth rinse pumps. In particular the plunger pump should have a drive for the piston that is as low wearing as possible. Also, the life of the piston and the seal should be increased.

Figure 19:
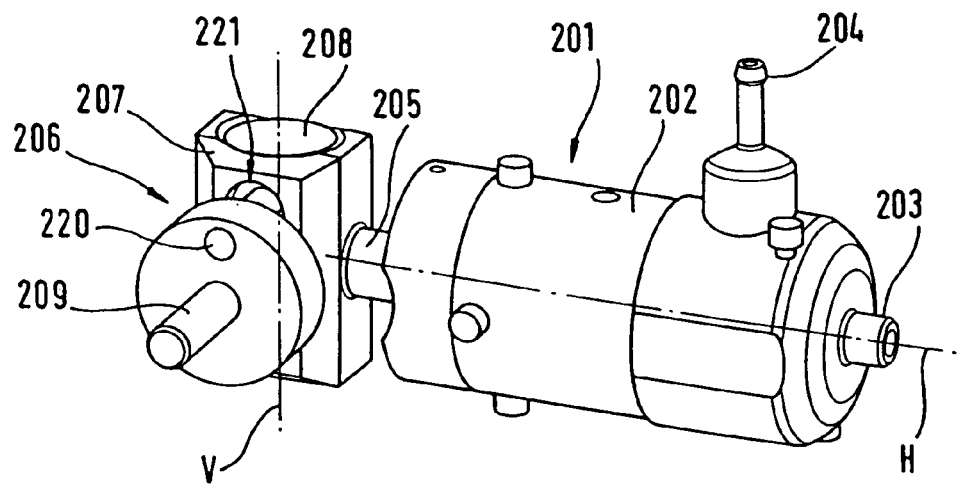
FIG. 19 is a perspective view of a plunger pump illustrating a first embodiment.

The plunger pump 201 of FIG. 19 has a pump housing 202 with an axially arranged pump inlet 203 and a radially arranged pump outlet 204. At the opposite end of the plunger pump 201 a piston 205 extends through the pump housing 202. The piston 205 is driven by an eccentric drive 206 or crank mechanism. The piston 205 has a sliding-block guideway 207 which receives a sliding block 208. To move the piston 205 a drive shaft 209 of the eccentric drive 206 or crank mechanism is set in rotation by an electric motor not shown.

Figure 20:
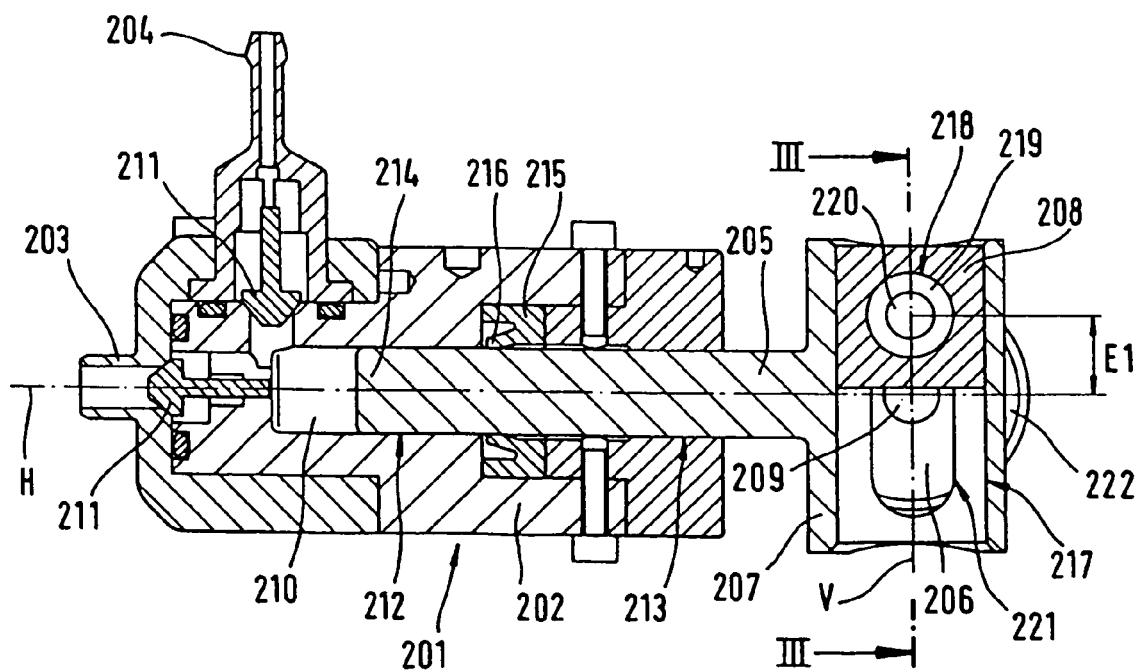
FIG. 20 is a sectional view of the plunger pump of FIG. 19.

The inner architecture of the plunger pump 201 with the pump chamber 210 is shown in FIG. 20. The pump chamber 210 has, with pump inlet 203 and pump outlet 204, two ports, with a non-return valve 211 associated with each. The one or several non-return valves 211 can be of the spring-loaded type. The non-return valves 211 are configured such that when the piston 205 moves out of the pump chamber 210 the non-return valve 211 in the pump inlet 203 opens while the non-return valve 211 in the pump outlet 204 is closed. During this movement of the piston 205, liquid is drawn from a container, not shown, in the mouth rinse, through the pump inlet 203 and into the pump chamber 210. When the piston 205 moves in the opposite direction, the action of the non-return valves 211 is reversed and the liquid is conveyed through the pump outlet 204 to a hand piece, not shown, of the mouth rinse.

The piston 205 is mounted in two bearings 212, 213 that are situated in the pump housing 202. In addition to being axially movable, the piston 205 is also arranged to be rotatable about its longitudinal axis H. The bearing 212 on the pump chamber 210 is constructed such that the piston end 214 is guided during a stroke between top and bottom dead center. The bearing 213 is situated at the other end of the pump housing 202. A seal 215 is fixedly arranged in the pump housing 202 centrally between the two bearings 212, 213. In this arrangement a sealing lip 216 seals off the piston 205. Arranged at the other end of the piston 205 is the sliding-block guideway 207. The sliding-block guideway 207 has a bore 217 in which the cylindrical sliding block 208 is arranged.

The slider or sliding block 208 is both axially movable as well as rotatable about the axis V. Owing to the rotary arrangement of the piston 205 and the slider or sliding block 208 about the axes H and V, the piston 205 is connected to a crankpin 220 of the eccentric drive 206 (or the crankpin 110 of the eccentric drive 101) in a practically cardan-type fashion, the only difference being that the piston 205 rotates about the axis H instead of being pivoted about an axis perpendicular to the two axes H and V. The piston 205 and this cardan or cardan-type connection enables a spatially skewed arrangement of the crankpin 220, which occurs as the result of tolerances or elastic and/or plastic or other deformations, to be compensated for.

A cardan connection in the sense of this description results when the piston 205 and the sliding block are rotatable and pivotal, respectively, about different axes H, V, with the two axes H and V extending perpendicular to each other.

The sliding block 208 has a bore 218 that extends transverse to the axis V and in which a bearing bushing 219 is inserted. The bearing bushing 219 is designed to receive the crankpin 220. For it to be received in the sliding block 208 the crankpin 220 has to penetrate the sliding-block guideway 207. For this purpose the sliding-block guideway 207 has an elongated hole 221. The width of the elongated hole 221 is larger than the crankpin diameter. Contact of the crankpin 220 with the sliding-block guideway 207 is thus ruled out. The width is selected such that no contact takes place even with a spatially skewed arrangement of the crankpin 220.

To drive the piston 205 the crankpin 220 moves on a circular path. In the presentation shown the crankpin 220 and the sliding block 208 are at top dead center. By contrast, the piston 205 lies exactly centrally between its two reversing points which limit its stroke. During a movement of the crankpin 220 in clockwise direction, the sliding block 208 moves downward in the sliding-block guideway 207 during the first half rotation. After a quarter rotation of the crankpin 220 the piston 205 reaches its rear reversing point which terminates the intake operation. Up to this moment the non-return valve 211 in the pump inlet 203 is open while the other non-return valve 211 is closed. During the second quarter rotation of the crankpin 220 the piston 205 moves again in the direction of the pump chamber 210. The non-return valve 211 in the pump inlet 203 is closed while the non-return valve 211 in the pump outlet 204 is open. After a half rotation the crankpin 220 mounted in the sliding block 208 reaches bottom dead center. The piston 205 is in the position shown. During the second half rotation of the crankpin 220 the sliding block 208 is again moved up, whereby after half of this movement the piston 205 reaches its front reversing point which terminates the discharge operation. It should be noted that springs for biasing the non-return valves 211 are not shown in FIG. 20.

Figure 21:
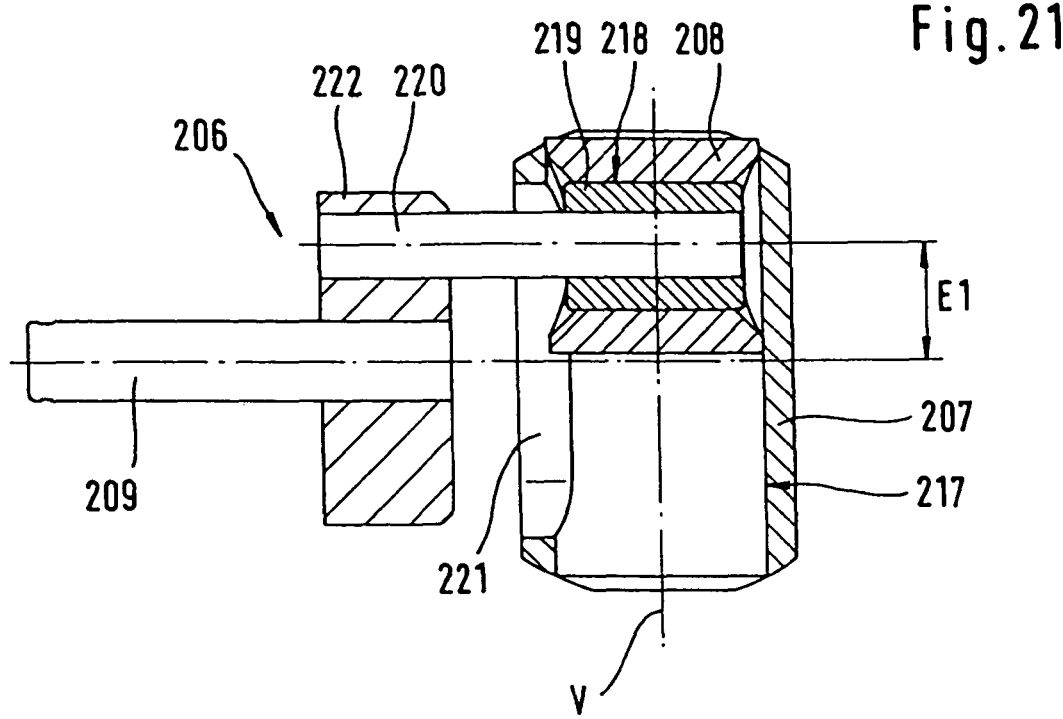
FIG. 21 is a sectional view of the plunger pump of FIG. 19 in the area of the eccentric drive.

FIG. 21 shows the crank mechanism 206 with the sliding-block guideway 207 of the piston 205. The crank mechanism 206 has a drive shaft 209 to which a disk 222 is fastened. The disk 222 carries the crankpin 220 which is arranged with the eccentricity E1. The crankpin 220 reaches through the elongated hole 221 of the sliding-block guideway 207 and into the sliding block 208 where it is received in a bearing bushing 219.

Figure 22:
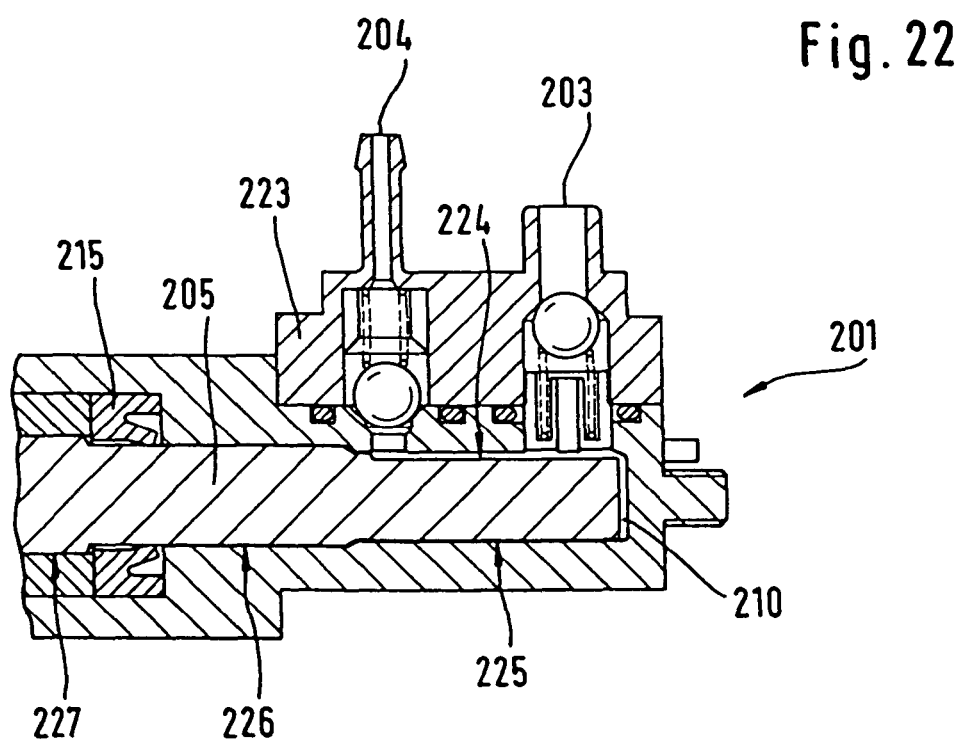
FIG. 22 is a sectional view of a second embodiment of a plunger pump in the region of the pump chamber, with the arrangement of piston and crank being exchanged compared to FIG. 19.
Figure 23:
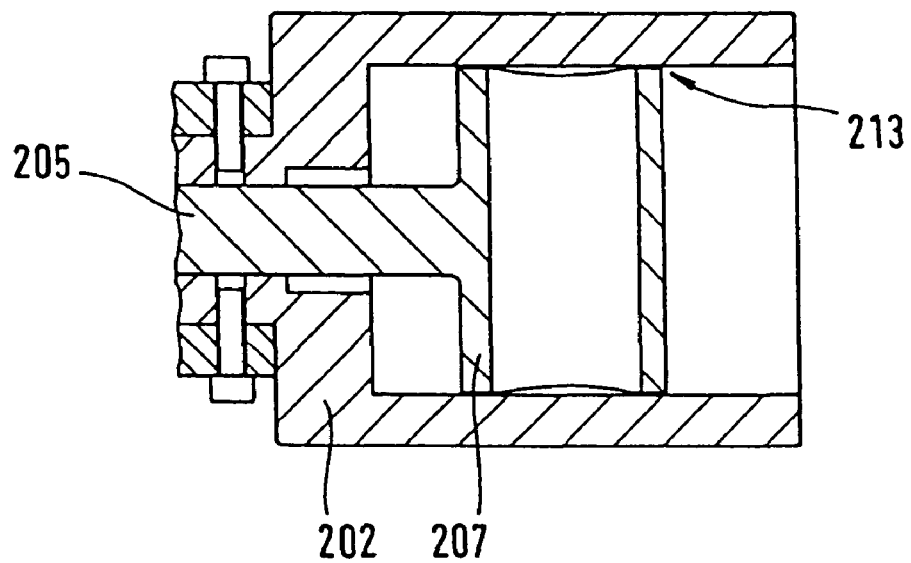
FIG. 23 is a schematic part-sectional view of an embodiment of the arrangement of a possible bearing.
Figure 24:
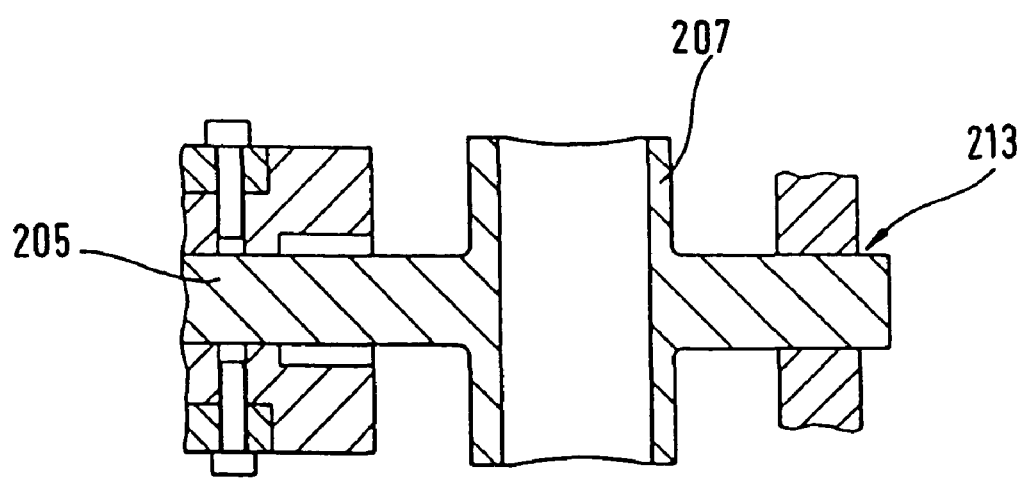
FIG. 24 is a schematic part-sectional view of another embodiment of the arrangement of a possible bearing.

The plunger pump 201 of a second embodiment in FIG. 22 shows the arrangement of the pump outlet 204 behind the pump inlet 203, both ports being radially arranged on the circumference of the plunger pump 201. The ports 203, 204 are integrated in a pressure piece 223 which is mounted on the plunger pump 201. The piston 205 has a flattening 224 on its side close to the pump inlet 203 and the pump outlet 204. The flattening 224 guarantees a communication of the pump outlet 204 with the pump chamber 210 which is independent of the position of the piston 205. In this embodiment, both non-return valves 211 are loaded or biased by a respective spring.

The piston 205 has three regions with different diameters 225-227, the diameters increasing from the bearing 212 through the region of the seal 215 to the bearing 213 which is no longer shown. With these steps 225-227 of piston diameter, any wear particles which arise are prevented from being distributed into the regions of the seal or the bearings.

Such a pump can be used not only in every mouth rinse but also in other fields including, for example, irrigation systems. It can be used basically in all pump devices with piston guidance.

Other Aspects of the Cleaning Process and of the Mouth Rinse

The mouth rinse preferably has two functions (operating modes) or two different, optionally usable spray nozzles. One function serves as a conventional mouth rinse with a low pressure of preferably around 4 to 8 bar, particularly around 6 bar (high-pressure function=around 45 bar). In this case microsized drops (spray function) are formed. The velocity of the discharged cleaning liquid is low. (This velocity lies preferably below 20 m/s, particularly in the range from 10 m/s to 15 m/s.) The flow rate with this mouth rinse function equals at least 100 mL/min, particularly 200 ml/min to 400 ml/min, preferably around 300 ml/min. The other high-pressure function was already described in detail.

The different functions are enabled by the switchable eccentric device or two variously long stroke travels of the pump.

One of the two functions can be optionally set. One function is practically a mouth rinse function, the other a new special function for the removal of dental plaque which can be compared with cleaning teeth using a toothbrush or has a comparable cleaning effect. This special function can at least reduce the use of a toothbrush and thus avoid severe abrasion.

The special function can also exist in an independent apparatus without a mouth rise function. A station with two such different mouth rinses, i.e., one mouth rinse with low pressure (as one apparatus) and one high-pressure mouth rinse as another apparatus, is also conceivable, whereby both apparatuses can use the same or different pumps.

In the special function (high-pressure spray mode) provision is made preferably for a high-pressure piston pump which reaches preferably a maximum of around 50 to 70 bar, particularly around 60 bar. One of the above described pressure ranges is also possible. The flow rate equals preferably around 50 to 70 ml/min, particularly 60 ml/min. The working distance between tooth and nozzle outlet equals around 2-6 mm. These values have proven themselves in particular in clinical studies.

Such a dual-function system enables particularly effective dental care. While the teeth are cleaned of coarse particles of dirt and the blood supply to the gums stimulated with the actual mouth rinse, subsequent cleaning with the high-pressure spray nozzle ensures that the teeth are thoroughly cleaned. The system can also include an electric toothbrush.

Figure 25:
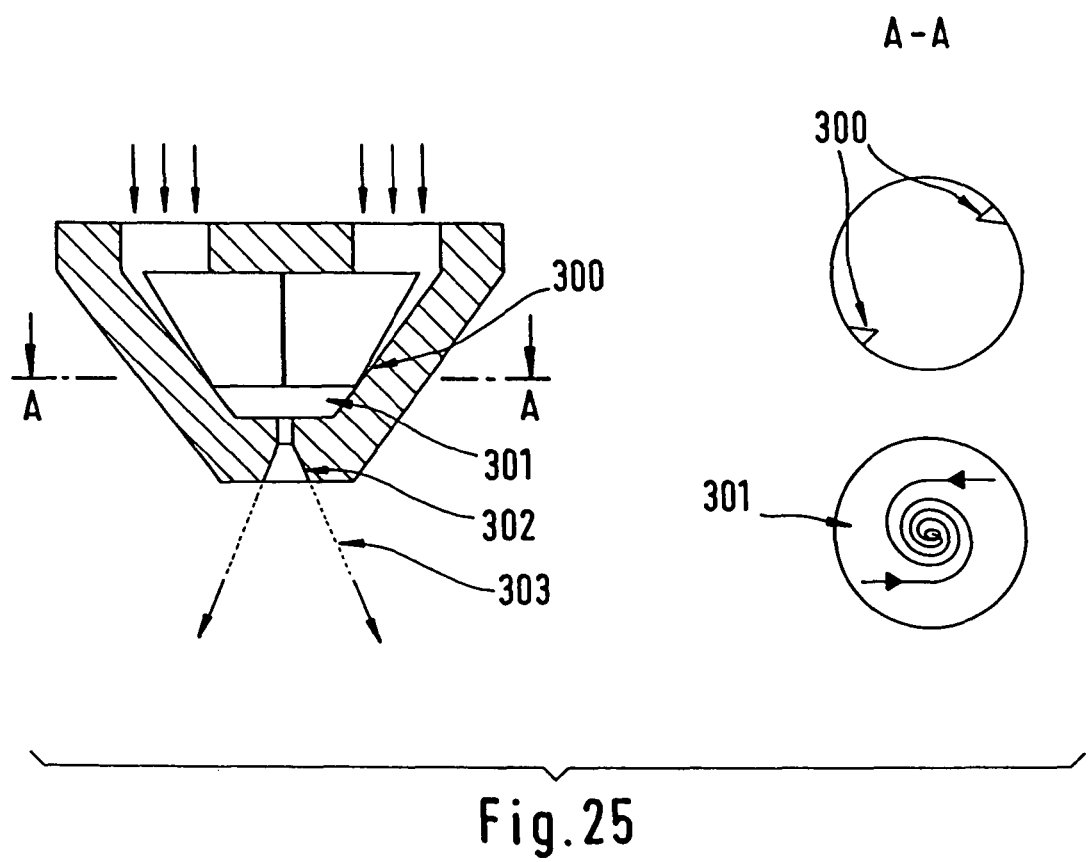
FIG. 25 is another view of a spray nozzle.

FIG. 25 illustrates once again the spray function or the special spray nozzle. The arrow 300 designates the eccentrically arranged slits which create the water whirl. The arrow 301 points to the whirl chamber with rotating water. The arrow 302 points to the rotating water which forms a thin water film along the conical nozzle outlet. The water film (arrow 303) is transformed into microsized drops at the exit.

The size of the drops can be changed by the geometry of the slits and/or the distance of the slits from the middle of the whirl chamber and/or by the angle and/or length of the outlet cone.

Figure 26:
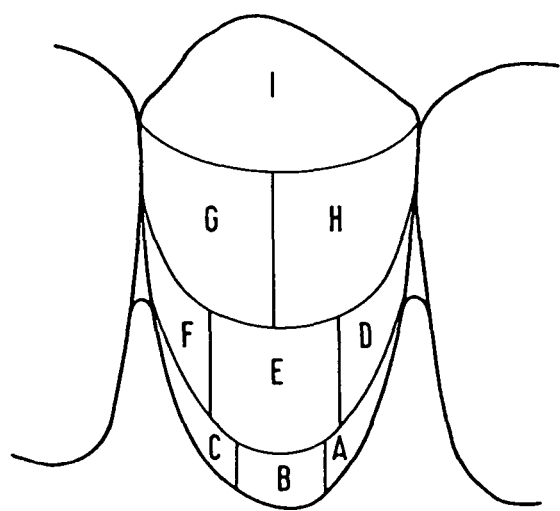
FIG. 26 is a view of segments of a tooth.

FIG. 26 shows the segments of a tooth according to "Rustogi". After just two minutes of cleaning time per dentition with the mouth rinse, more than 70% to 80% of the plaque is removed in the approximal regions (D and F) and in the gingival margins (A, B and C). In the other regions (I, G, H and E) there is an even better cleaning effect. Cleaning also occurs in the proximal regions (spaces between the teeth). In this case the cleaning causes very little abrasion, being very gentle on the teeth.

Figure 29:
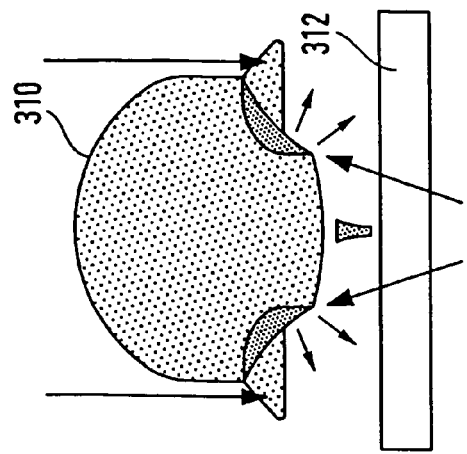
FIG. 29 is a view as in FIG. 28, but upon plaque removal.
Figure 28:
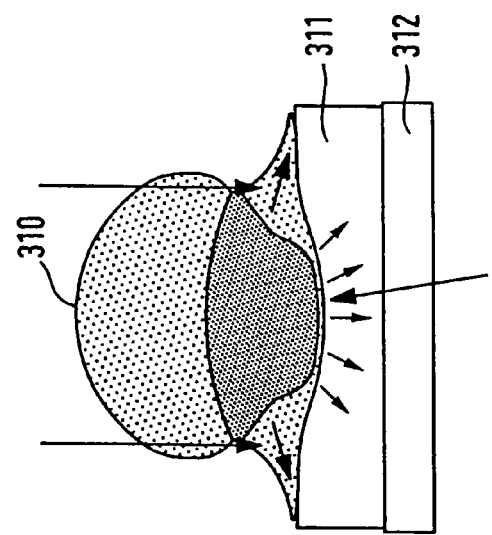
FIG. 28 is a view as in FIG. 27, but at a later instant.
Figure 27:
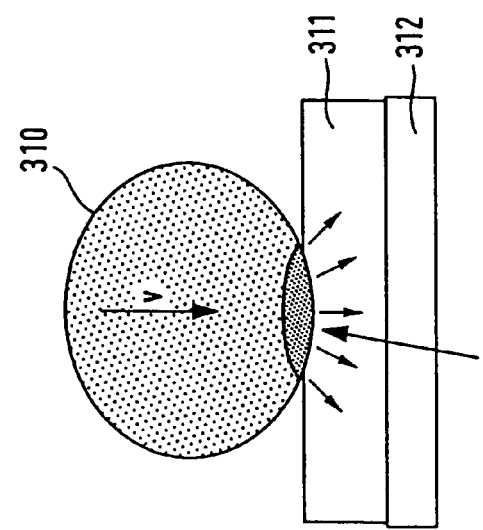
FIG. 27 is a view of a drop as it impinges on plaque.

FIGS. 27 to 29 show the cleaning process with reference to a microsized drop 310. This drop impacts in pulse-like manner with high energy on a plaque layer 311 on a tooth 312 (FIG. 27). This energy causes the plaque to be forced outward (FIG. 28), whereby a high pressure prevails in the middle of the drop. A crater develops. The pressure shifts outward, as is illustrated by the two upward pointing arrows of FIG. 29.

Figure 32:
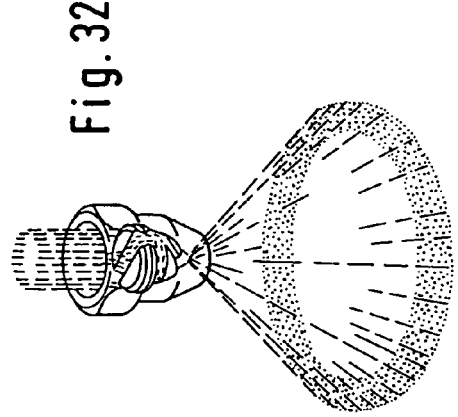
FIG. 32 is a perspective view of a spray nozzle illustrating a still further embodiment.
Figure 31:
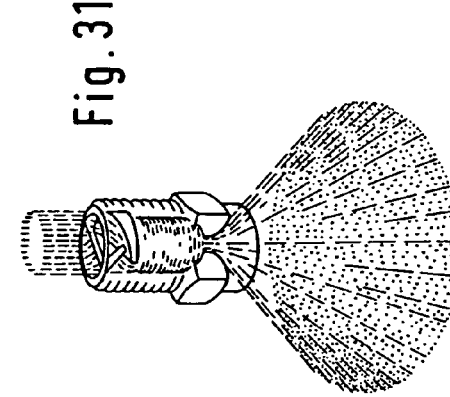
FIG. 31 is a perspective view of a spray nozzle illustrating another embodiment.
Figure 30:
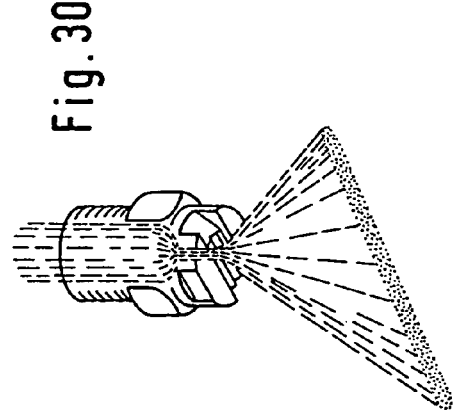
FIG. 30 is a perspective view of a spray nozzle.

FIGS. 30 to 32 show further embodiments of the spray nozzle which are adapted to be combined with the features of one or several of the above described nozzles.

The spray nozzle of FIG. 30 produces a flat, expanding jet. FIG. 31 shows a spray nozzle with a solid cone jet. FIG. 32 shows a spray nozzle with a hollow cone jet, with which a very gentle cleaning effect can be achieved, the volume of water being small.

Figure 33:
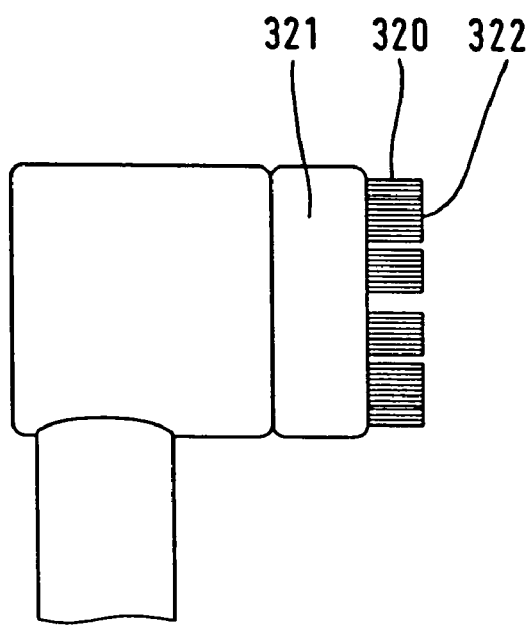
FIG. 33 is a side view of a brush element.
Figure 34:
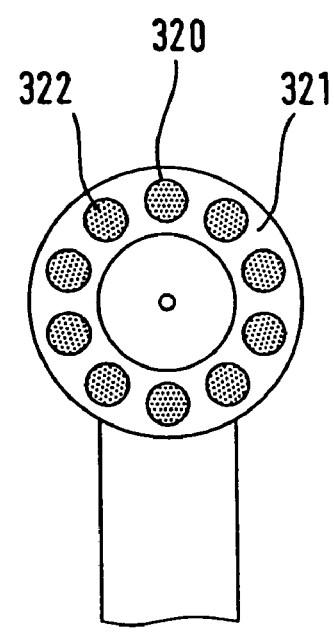
FIG. 34 is a front view of the brush element.

FIGS. 33 and 34 show a spray nozzle with a nozzle attachment that is constructed preferably as a ring-shaped brush 320—comprising preferably a plastic ring 321 and bristles 322 arranged in sectors. Said nozzle attachment can be fixedly or releasably arranged on the nozzle head. Apart from enhancing the cleaning effect the ring-shaped brush has the added effect of a spacer element such that a defined (safety) distance exists between the tooth and the nozzle opening. Also conceivable is a function by which the ring-shaped brush rotates, being in particular driven in alternating fashion in two directions of rotation similar to an electric toothbrush, e.g., by means of an electric drive, particularly a motor drive. However, other movement sequences and brush forms are also possible. A brushless element can also serve as a spacer element. The brush-type nozzle attachment can also be used for a known low-pressure mouth rinse.

It will be understood that the dental cleaning system is not limited to the examples described. Any combination of the individual features of the various examples is possible. In particular the combination of a mouth rinse according to FIGS. 1 to 7 with an eccentric drive according to FIGS. 8 to 18 and/or with a pump according to FIGS. 19 to 24 is suitable.

The invention claimed is:

1. A spray nozzle for a mouth rinse, the spray nozzle comprising:
    a nozzle member;
    a nozzle attachment couple to the nozzle member to define an axially extending chamber;
    a liquid duct configured to supply pressurized liquid to the chamber;
    a pressure piece disposed within the chamber;
    a whirl chamber connected to the chamber, the whirl chamber being configured to create a circulating flow of the liquid; and
    a nozzle outlet formed in the nozzle attachment and extending centrally from the whirl chamber and configured to discharge a cleaning jet, the nozzle outlet comprising a substantially cylindrical narrow passage;
    wherein a first end of the pressure piece comprises a cup-shaped portion having grooves extending from the chamber to openings;
    wherein a second end of the pressure piece, opposite the first end, comprises a second cup-shaped portion including an interior space in fluid communication with the liquid duct as well as with the chamber;
    wherein the interior space of the second end of the pressure piece communicates with the chamber through at least one opening which is constructed as an axial slit; and
    wherein a plurality of axial slits along the second end of the pressure piece define a plurality of spring arms to axially and resiliently secure the pressure piece in the chamber.

2. The spray nozzle of claim 1, wherein the nozzle outlet is sized and configured such that a velocity of the cleaning jet is at least about 23 m/s.

3. The spray nozzle of claim 1, wherein the nozzle outlet is sized and configured such that the cleaning jet is a diverging hollow cone jet.

4. The spray nozzle of claim 1, wherein the liquid duct is sized and configured to supply pressurized liquid to the chamber at a pressure of at least about 15 bar.

5. The spray nozzle of claim 1, wherein the liquid duct is sized and configured to supply pressurized liquid to the chamber at a pressure between about 25 bar and about 55 bar.

6. The spray nozzle of claim 1, wherein the liquid duct is sized and configured to supply pressurized liquid to the chamber at a pressure between about 35 bar and about 45 bar.

7. The spray nozzle of claim 1, further comprising openings extending into the whirl chamber along a substantially transverse direction and with a center offset relative to the longitudinal axis of the whirl chamber, such that the cleaning jet exiting from the openings impacts an opposite wall of the whirl chamber at an angle not exceeding about 45°.

* * * * *